(12) United States Patent
Ivosevic et al.

(10) Patent No.: US 12,193,817 B2
(45) Date of Patent: Jan. 14, 2025

(54) BIOLOGICAL FLUID COLLECTION DEVICE

(71) Applicant: Becton, Dickinson and Company, Franklin Lakes, NJ (US)

(72) Inventors: Milan Ivosevic, Kinnelon, NJ (US); Ryan W. Muthard, Wynnewood, PA (US); Alexander James Blake, Ridgewood, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 513 days.

(21) Appl. No.: 16/630,344

(22) PCT Filed: Jul. 6, 2018

(86) PCT No.: PCT/US2018/041027
§ 371 (c)(1),
(2) Date: Jan. 10, 2020

(87) PCT Pub. No.: WO2019/014054
PCT Pub. Date: Jan. 17, 2019

(65) Prior Publication Data
US 2021/0153793 A1    May 27, 2021

Related U.S. Application Data

(60) Provisional application No. 62/532,111, filed on Jul. 13, 2017.

(51) Int. Cl.
*A61B 5/15*    (2006.01)
(52) U.S. Cl.
CPC .. *A61B 5/150343* (2013.01); *A61B 5/150022* (2013.01); *A61B 5/15003* (2013.01); *A61B 5/150755* (2013.01)

(58) Field of Classification Search
CPC ........ A61B 5/150343; A61B 5/150022; A61B 5/15003; A61B 5/150755;
(Continued)

(56) References Cited

U.S. PATENT DOCUMENTS 4,091,802 A * 5/1978 Columbus ............. B01L 3/5021
422/918
4,280,496 A * 7/1981 Van Baelen ..... A61B 5/150732
604/83

(Continued)

FOREIGN PATENT DOCUMENTS

| CN | 101695447 A | 4/2010 |
| CN | 205083491 U | 3/2016 |

(Continued)

*Primary Examiner* — Yi-Shan Yang
*Assistant Examiner* — Om Patel
(74) *Attorney, Agent, or Firm* — The Webb Law Firm

(57) ABSTRACT

A biological fluid collection device (10) that produces a stabilized biological sample with head-to-tail uniformity through the capturing of a high concentration front and subsequent redistribution of the high concentration front throughout a biological fluid is disclosed. The biological fluid collection device includes an inline mixer (16) used for head-to-tail mixing of a concentrated flow front. The mixing is achieved via a two-stage process. First, a front fraction of the flow is captured within a centered mixing chamber (30) via capillary assisted flow action. Second, the captured front volume is then slowly released throughout a small exit hole (36) and recombined with the rest of the flow volume that was diverted around the centered mixer chamber.

27 Claims, 19 Drawing Sheets

(58) Field of Classification Search
CPC ........ A61B 5/150221; A61B 5/150101; A61B 5/150778; A61B 5/150351; A61B 5/150267; A61B 5/150213; A61B 5/15144; A61B 5/157; A61B 5/150412; A61B 5/150748; A61B 5/150969; A61B 5/150435; A61B 5/150305; A61B 5/15–150045; B01F 25/00; B01F 25/4323; B01F 25/432–4423; A61M 16/0497; A61M 1/3673; A61L 33/0011
See application file for complete search history.

(56) References Cited

U.S. PATENT DOCUMENTS

| | | | |
|---|---|---|---|
| 5,141,501 A * | 8/1992 | Atkinson | A61M 1/3672 604/20 |
| 6,511,439 B1 | 1/2003 | Tabata et al. | |
| 2010/0103768 A1 * | 4/2010 | Gordon | B01F 25/4335 366/165.4 |
| 2014/0099646 A1 * | 4/2014 | Connolly | C12M 47/06 435/6.12 |
| 2014/0305823 A1 | 10/2014 | Gelfand et al. | |
| 2014/0308164 A1 | 10/2014 | Wilkinson et al. | |
| 2014/0308165 A1 | 10/2014 | Marchiarullo et al. | |
| 2014/0336536 A1 | 11/2014 | Brancazio | |
| 2015/0164398 A1 | 6/2015 | Ko et al. | |
| 2016/0100783 A1 | 4/2016 | Ivosevic et al. | |
| 2016/0103046 A1 * | 4/2016 | Ivosevic | A61B 5/150343 422/549 |
| 2016/0262679 A1 | 9/2016 | Ivosevic et al. | |
| 2016/0367177 A1 * | 12/2016 | Edelhauser | A61B 5/15003 |
| 2017/0035337 A1 | 2/2017 | Wilkinson et al. | |

FOREIGN PATENT DOCUMENTS

| | | | | |
|---|---|---|---|---|
| CN | 105899133 A | | 8/2016 | |
| CN | 106604780 A | | 4/2017 | |
| GB | 2096911 | * | 10/1982 | |
| JP | 2001509884 A | | 7/2001 | |
| JP | 2001224575 A | | 8/2001 | |
| WO | 9818518 A1 | | 5/1998 | |
| WO | WO-2005014173 A1 | * | 2/2005 | ........... A61B 5/1438 |
| WO | WO-2010036387 A2 | * | 4/2010 | ........ A61B 10/0096 |
| WO | WO-2013059425 A1 | * | 4/2013 | ........ A61B 5/15003 |
| WO | 2014172233 A1 | | 10/2014 | |
| WO | 2014172234 A1 | | 10/2014 | |
| WO | 2014172247 A1 | | 10/2014 | |
| WO | 2017001922 A1 | | 1/2017 | |

* cited by examiner

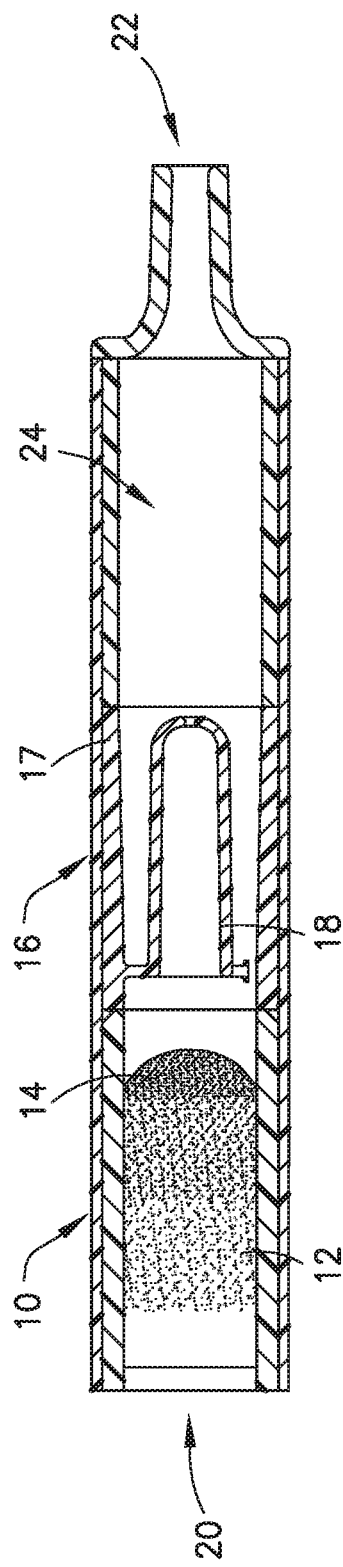
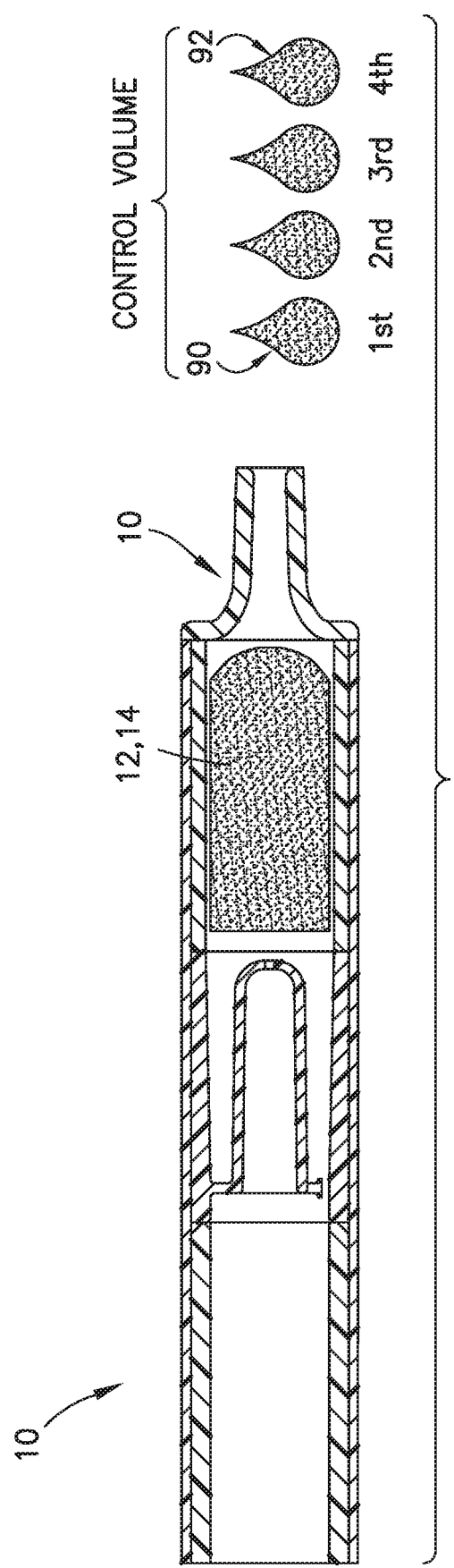
FIG.5
FIG.7

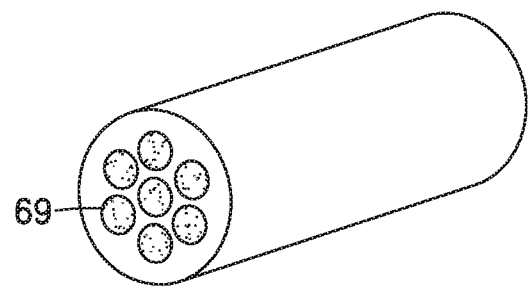
FIG.22
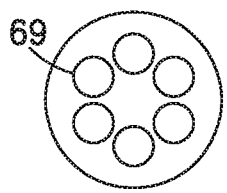 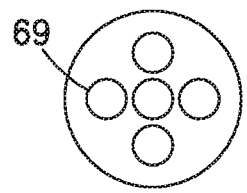 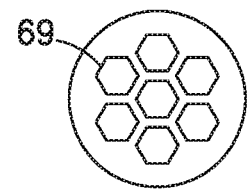
FIG.23   FIG.24   FIG.25
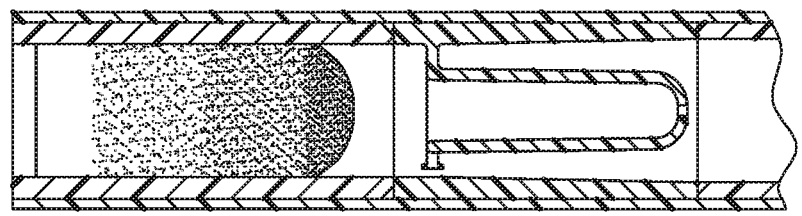
FIG.26

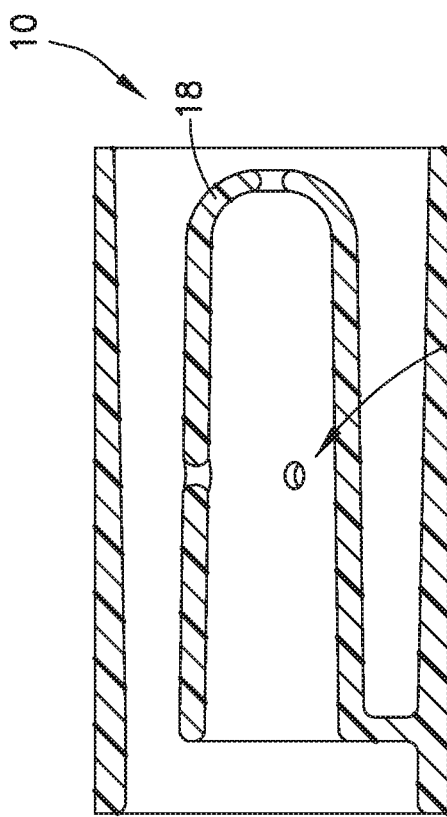
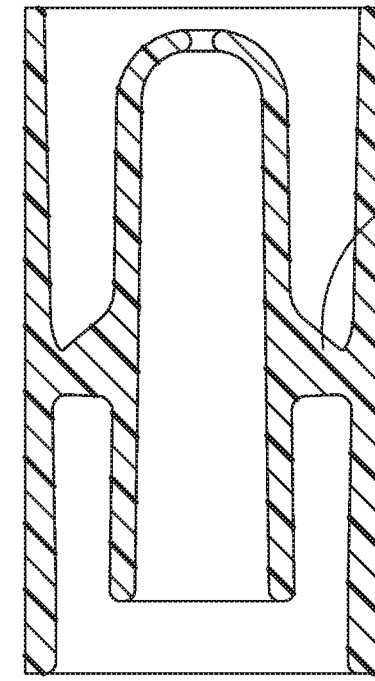
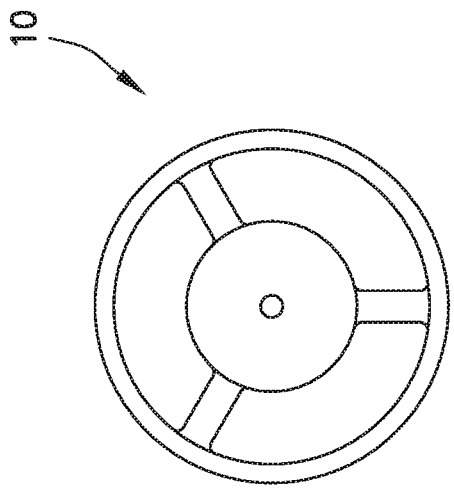
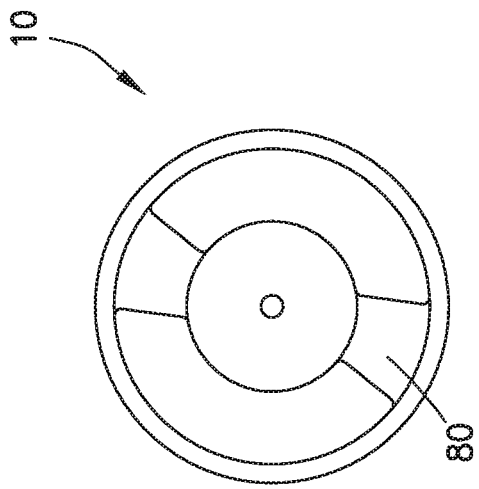

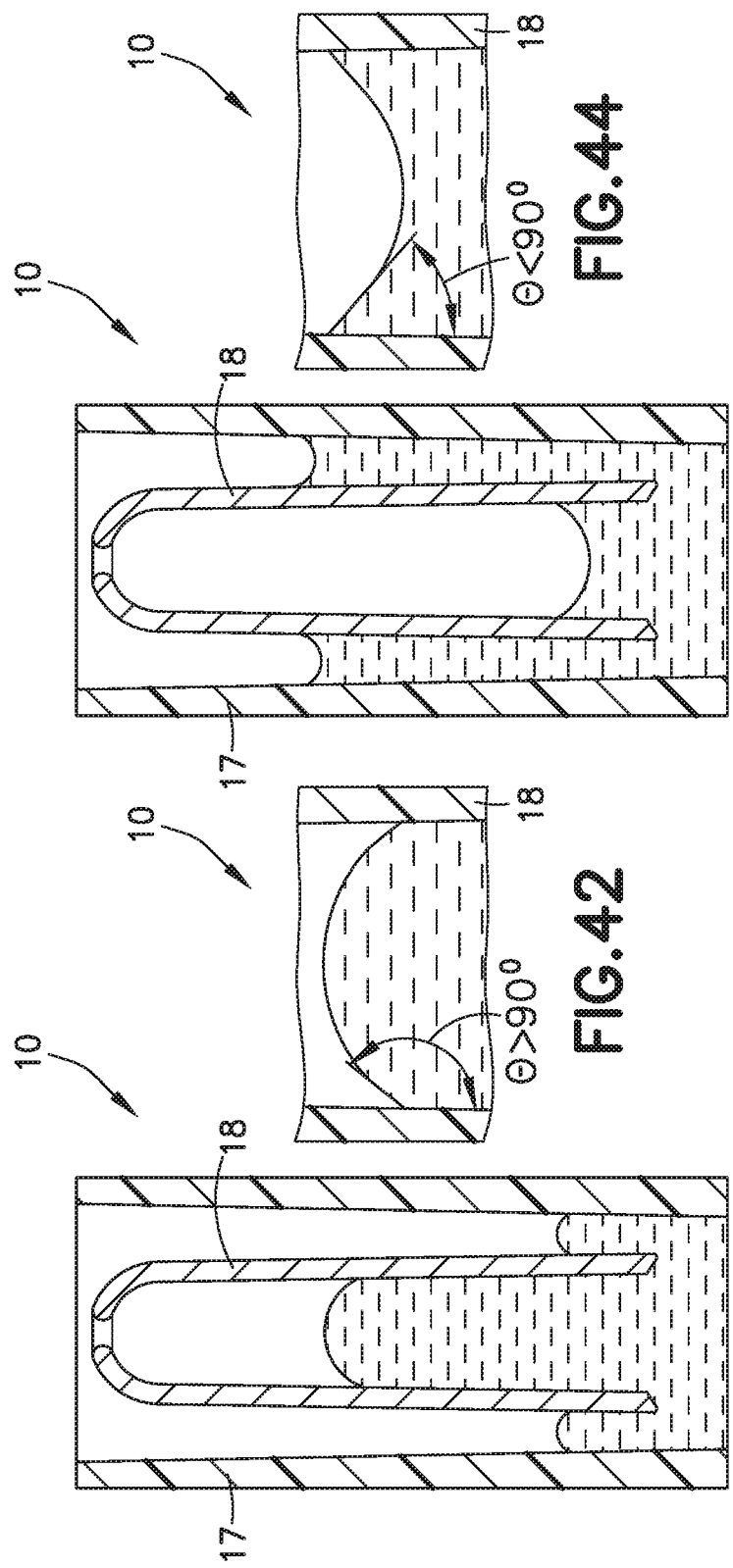

BIOLOGICAL FLUID COLLECTION DEVICE

CROSS-REFERENCE TO RELATED APPLICATIONS

This application is the United States national phase of International Application No. PCT/US2018/041027 filed Jul. 6, 2018, and claims priority to U.S. Provisional Application Ser. No. 62/532,111, entitled "Biological Fluid Collection Device", and filed Jul. 13, 2017, the entire disclosures of which are hereby incorporated by reference.

BACKGROUND OF THE INVENTION

1. Field of the Disclosure

The present disclosure relates generally to a biological fluid collection device. More particularly, the present disclosure relates to a biological fluid collection device that produces a stabilized biological sample with head-to-tail uniformity through the capturing of a high concentration front and subsequent redistribution of the high concentration front throughout a biological fluid.

2. Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Blood samples may also be taken from patients by venous or arterial lines. Once collected, blood samples may be analyzed to obtain medically useful information including chemical composition, hematology, and coagulation, for example.

Despite the rapid advancement in point-of-care testing and diagnostics, blood sampling techniques have remained relatively unchanged. Blood samples are frequently drawn using hypodermic needles or vacuum tubes attached to a proximal end of a needle or a catheter assembly. In some instances, clinicians collect blood from a catheter assembly using a needle and syringe that is inserted into the catheter to withdraw blood from a patient through the inserted catheter. These procedures utilize needles and vacuum tubes as intermediate devices from which the collected blood sample is typically withdrawn prior to testing. These processes are thus device intensive, utilizing multiple devices in the process of obtaining, preparing, and testing blood samples. Each additional device increases the time and cost of the testing process. Furthermore, mixing with an anticoagulant or other component to stabilize the sample must be performed manually.

Point-of-care testing devices allow for a blood sample to be tested without needing to send the blood sample to a lab for analysis. Thus, it is desirable to create a device that provides an easy, safe, reproducible, and accurate process with a point-of-care testing system.

Point-of-care devices and devices devised to transfer a sample from the patient to the point-of-care device often accept samples which have been taken freshly from the patient, without stabilization. In these instances, anything happening to the blood after collection would be entirely inside the cartridge and without any liquid-handling by the user. A concern in such devices is how the additive, e.g., an anticoagulant, when included as part of the manufactured device, will dissolve and be picked up by the incoming blood stream. There is a high likelihood that the first blood flowing into and through the device will pick up a majority, if not perhaps all, of the anticoagulant, resulting in a very high anticoagulant concentration in this first volume, and too low or perhaps no anticoagulant in the later volumes of blood. This effect is likely, especially with heparin which is highly soluble. The outcomes of this effect result in several complications that could reduce device utility if not actually prevent device function. High levels of anticoagulant can induce hemolysis and underdosing of anticoagulant can lead to clotting, which may plug microfluidic devices, adding a mechanical/fluidic complication in addition to the well-known preanalytical complications typical of clotting/microclotting.

SUMMARY OF THE INVENTION

The present disclosure provides a biological fluid collection device that produces a stabilized biological sample with head-to-tail uniformity through the capturing of a high concentration front and subsequent redistribution of the high concentration front throughout a biological fluid. The biological fluid collection device includes an inline mixer used for head-to-tail mixing of a concentrated flow front. The mixing is achieved via a two-stage process. First, a front fraction of the flow is captured within a centered mixing chamber via capillary assisted flow action. Second, the captured front volume is then slowly released throughout a small exit hole and recombined with the rest of the flow volume that was diverted around the centered mixer chamber.

In accordance with an embodiment of the present invention, a biological fluid collection device includes an inlet portion; an outlet portion; an outer wall spanning the inlet portion and the outlet portion; an inner wall disposed within an interior portion of the outer wall and spaced from the outer wall, the inner wall defining a chamber therein and including a first end and a second end, the first end in fluid communication with the inlet portion and the second end defines an exit aperture; a flow channel disposed between the outer wall and the inner wall, the flow channel in fluid communication with the inlet portion; a mixing portion disposed between the second end of the inner wall and the outlet portion; and a sample stabilizer disposed within a portion of the outer wall.

In one configuration, a distance between the inner wall and the outer wall is greater than a diameter of the exit aperture. In another configuration, the first end is open and defines a first cross-sectional area. In yet another configuration, the inner wall is secured to the outer wall via a connection portion. In one configuration, the sample stabilizer is disposed within a portion of the outer wall between the inlet portion and the first end of the inner wall. In another configuration, the outer wall at the inlet portion has a first diameter, and a first portion of the outer wall between the inlet portion and the first end of the inner wall has a second diameter, the second diameter is less than the first diameter. In yet another configuration, a second portion of the outer wall adjacent the inner wall has a third diameter, the third diameter is greater than the second diameter. In one configuration, the inlet portion is adapted to receive a blood sample therein. In another configuration, with the blood sample received within the inlet portion, the sample stabilizer mixes with the blood sample. In yet another configuration, a first additive front is created within a front portion of the blood sample. In one configuration, the front portion of the blood sample flows into the chamber of the inner wall and a rear portion of the blood sample flows into the flow channel. In another configuration, the front portion of the blood sample with the first additive front flows through the exit aperture to the mixing portion at a controlled rate back into the rear portion of the blood sample. In yet another configuration, the front portion of the blood sample with the first additive front flows through the exit aperture to the mixing portion back into the rear portion of the blood sample to effectuate metered mixing of the sample stabilizer within the front portion of the blood sample and the rear portion of the blood sample. In one configuration, the biological fluid collection device includes a material including pores and disposed within the interior of the outer wall, and the sample stabilizer comprises a dry anticoagulant powder within the pores of the material. In another configuration, the material is an open cell foam. In yet another configuration, the sample stabilizer comprises a dry anticoagulant powder disposed within the interior of the outer wall. In one configuration, the biological fluid collection device includes fins to promote rotational mixing. In another configuration, the inner wall defines a side exit aperture.

In accordance with another embodiment of the present invention, a biological fluid collection device includes an inlet portion; an outlet portion; an outer wall spanning the inlet portion and the outlet portion, the outer wall including a top wall and a bottom wall; a first inner wall disposed within the interior of the outer wall and spanning the top wall and the bottom wall, the first inner wall including a first inner wall first end and a first inner wall second end; a second inner wall disposed within the interior of the outer wall and spanning the top wall and the bottom wall, the second inner wall including a second inner wall first end and a second inner wall second end; a first flow channel disposed between a first portion of the outer wall and the first inner wall, the first flow channel in fluid communication with the inlet portion; a second flow channel disposed between a second portion of the outer wall and the second inner wall, the second flow channel in fluid communication with the inlet portion; a mixing portion disposed between the first inner wall second end and the outlet portion; and a sample stabilizer disposed within a portion of the outer wall, wherein the first inner wall and the second inner wall together define a chamber therebetween, the chamber in fluid communication with the inlet portion.

In one configuration, the first inner wall first end is spaced a first distance from the second inner wall first end and the first inner wall second end is spaced a second distance from the second inner wall second end, the second distance less than the first distance. In another configuration, the second distance defines an exit aperture. In yet another configuration, the first portion of the outer wall comprises a first sidewall and the second portion of the outer wall comprises a second sidewall. In one configuration, the sample stabilizer is disposed within a portion of the outer wall between the inlet portion and the first inner wall first end. In another configuration, the inlet portion is adapted to receive a blood sample therein. In yet another configuration, with the blood sample received within the inlet portion, the sample stabilizer mixes with the blood sample. In one configuration, a first additive front is created within a front portion of the blood sample. In another configuration, the front portion of the blood sample flows into the chamber and a rear portion of the blood sample flows into the first flow channel and the second flow channel. In yet another configuration, the front portion of the blood sample with the first additive front flows through the exit aperture to the mixing portion at a controlled rate back into the rear portion of the blood sample. In one configuration, the front portion of the blood sample with the first additive front flows through the exit aperture to the mixing portion back into the rear portion of the blood sample to effectuate metered mixing of the sample stabilizer within the front portion of the blood sample and the rear portion of the blood sample. In another configuration, the biological fluid collection device includes a material including pores and disposed within the interior of the outer wall, and the sample stabilizer comprises a dry anticoagulant powder within the pores of the material. In yet another configuration, the material is an open cell foam. In one configuration, the sample stabilizer comprises a dry anticoagulant powder.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 5 is a partial cross-sectional view of a biological fluid collection device with a mixer in accordance with an embodiment of the present invention.

FIG. 7 is a partial cross-sectional view of a biological fluid collection device with a mixer in accordance with an embodiment of the present invention.

FIG. 10 is a perspective view of a conventional biological fluid collection device.

FIG. 11 is a perspective view of a drop to drop concentration yielded by a conventional biological fluid collection device.

FIG. 12 is a perspective view of a biological fluid collection device with a mixer in accordance with an embodiment of the present invention.

Figure 13:
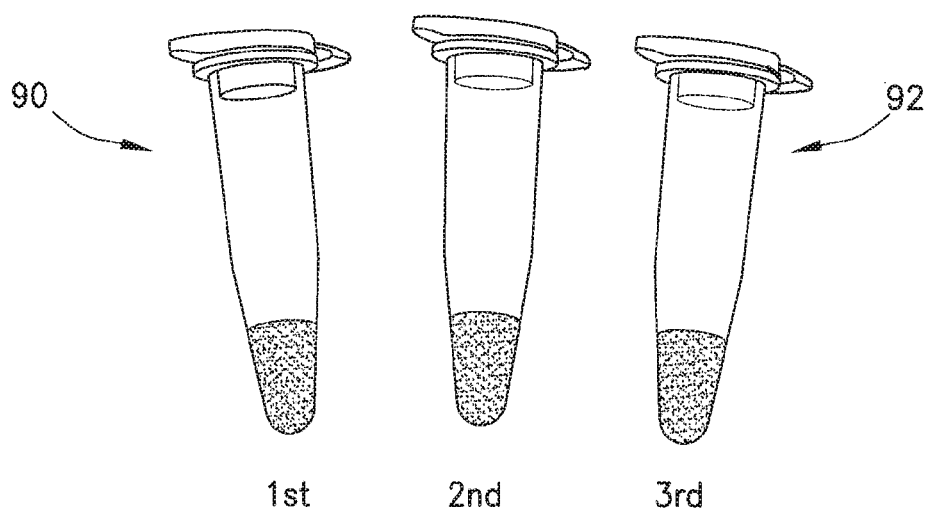

FIG. 13 is a perspective view of a drop to drop concentration yielded by a biological fluid collection device with a mixer in accordance with an embodiment of the present invention.

Figure 14:
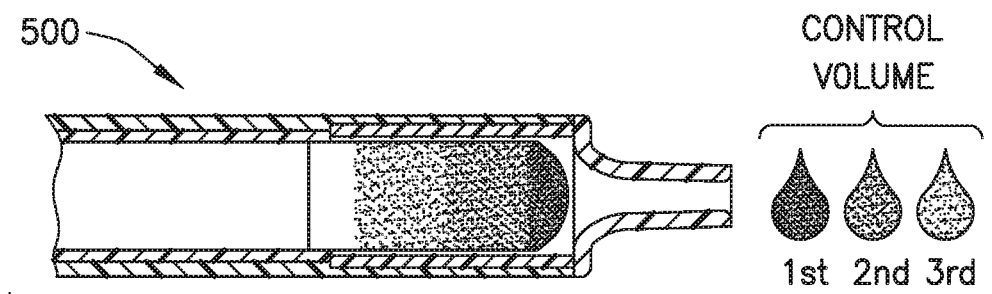

FIG. 14 is a partial cross-sectional view of a conventional biological fluid collection device.

Figure 15:
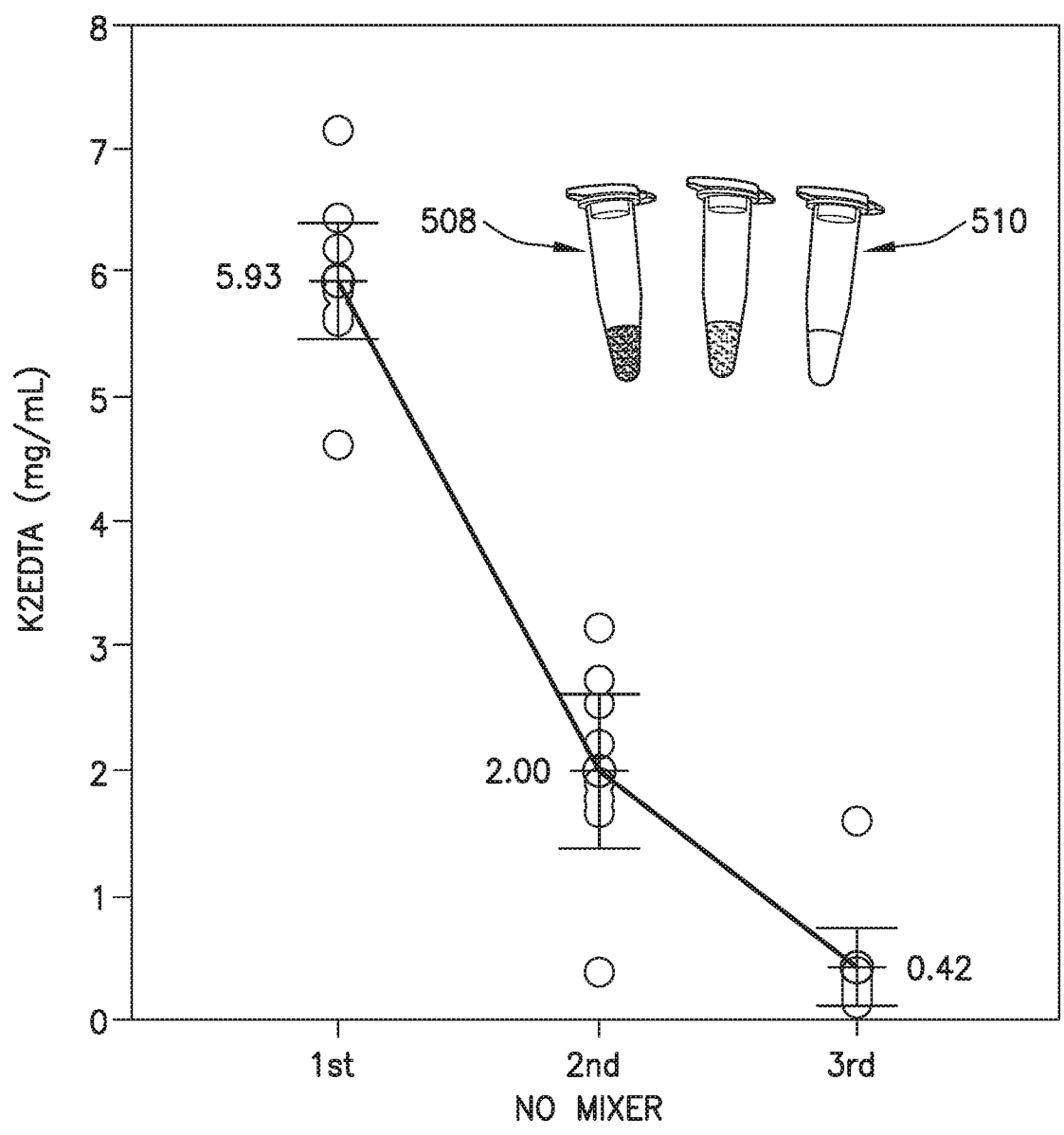

FIG. 15 is a graph of a drop to drop concentration yielded by a conventional biological fluid collection device.

Figure 16:
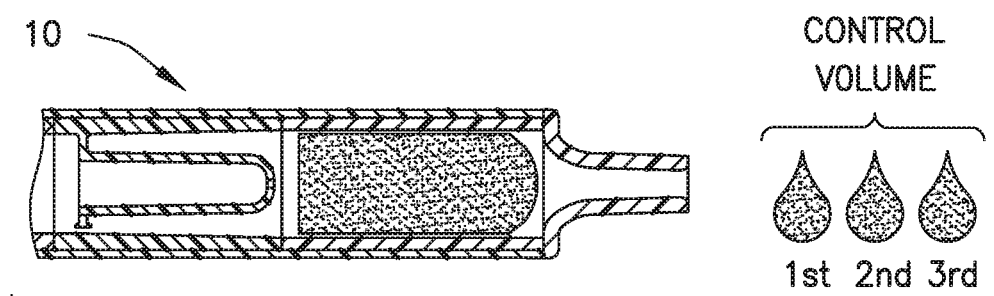

FIG. 16 is a partial cross-sectional view of a biological fluid collection device with a mixer in accordance with an embodiment of the present invention.

Figure 17:
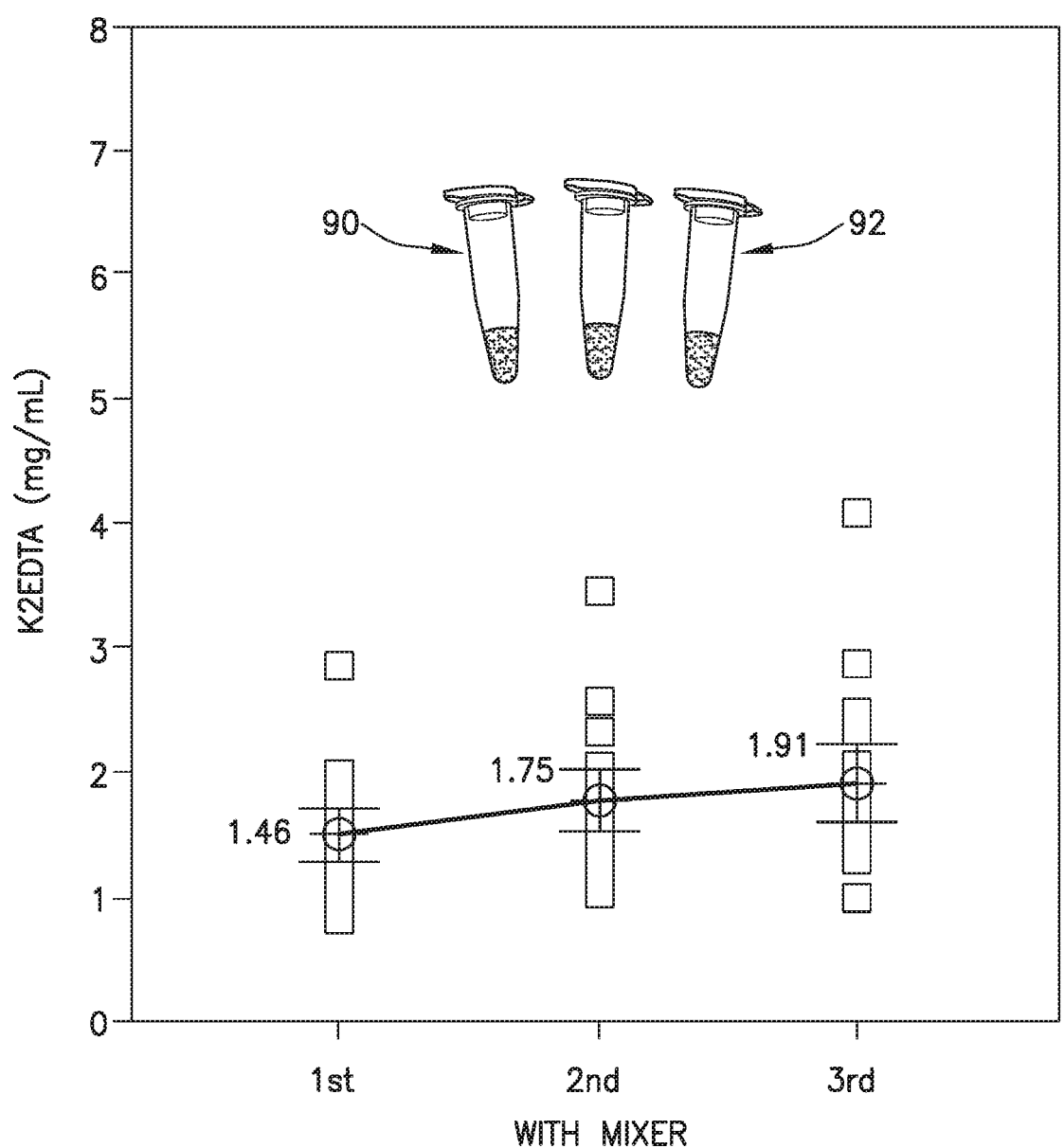

FIG. 17 is a graph of a drop to drop concentration yielded by a biological fluid collection device with a mixer in accordance with an embodiment of the present invention.

Figure 18:
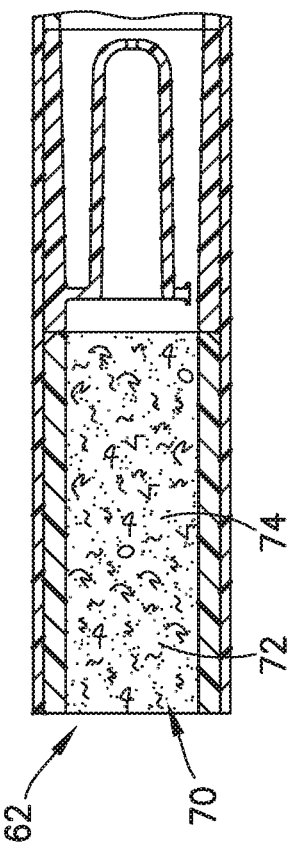

FIG. 18 is a partial cross-sectional view of a biological fluid collection device with a mixer and an internal wall coated with a dry additive in accordance with an embodiment of the present invention.

Figure 19:
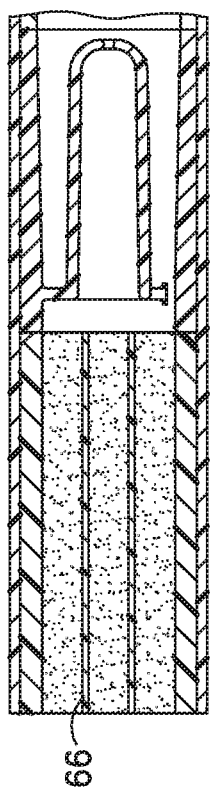

FIG. 19 is a partial cross-sectional view of a biological fluid collection device with a mixer and an open cell foam material in accordance with an embodiment of the present invention.

Figure 20:
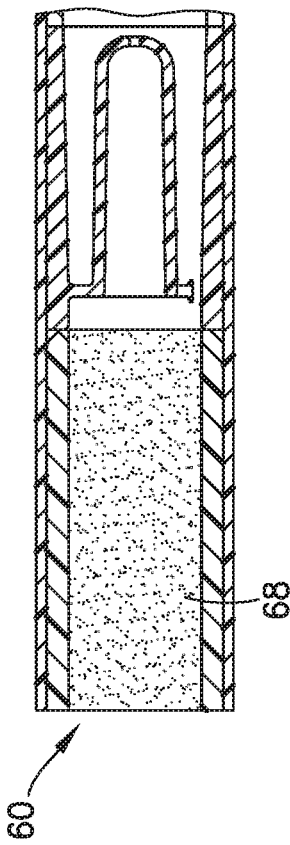

FIG. 20 is a partial cross-sectional view of a biological fluid collection device with a mixer and a plurality of beads coated with a dry additive in accordance with an embodiment of the present invention.

Figure 21:
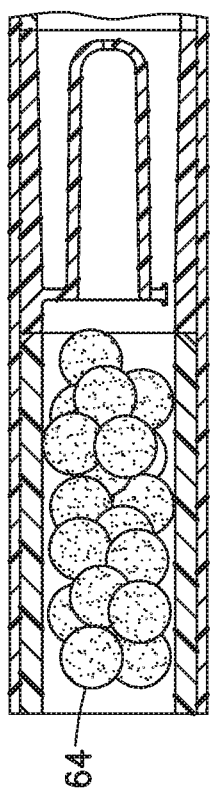

FIG. 21 is a partial cross-sectional view of a biological fluid collection device with a mixer and a three-dimensional structure coated with a dry additive in accordance with an embodiment of the present invention.

FIG. 22 is a perspective view of a three-dimensional structure coated with a dry additive in accordance with an embodiment of the present invention.

FIG. 23 is a front elevation view of a three-dimensional structure coated with a dry additive with a first geometric pattern in accordance with an embodiment of the present invention.

FIG. 24 is a front elevation view of a three-dimensional structure coated with a dry additive with a second geometric pattern in accordance with an embodiment of the present invention.

FIG. 25 is a front elevation view of a three-dimensional structure coated with a dry additive with a third geometric pattern in accordance with an embodiment of the present invention.

FIG. 26 is a partial cross-sectional view of a biological fluid collection device with a mixer in accordance with an embodiment of the present invention.

Figure 27:
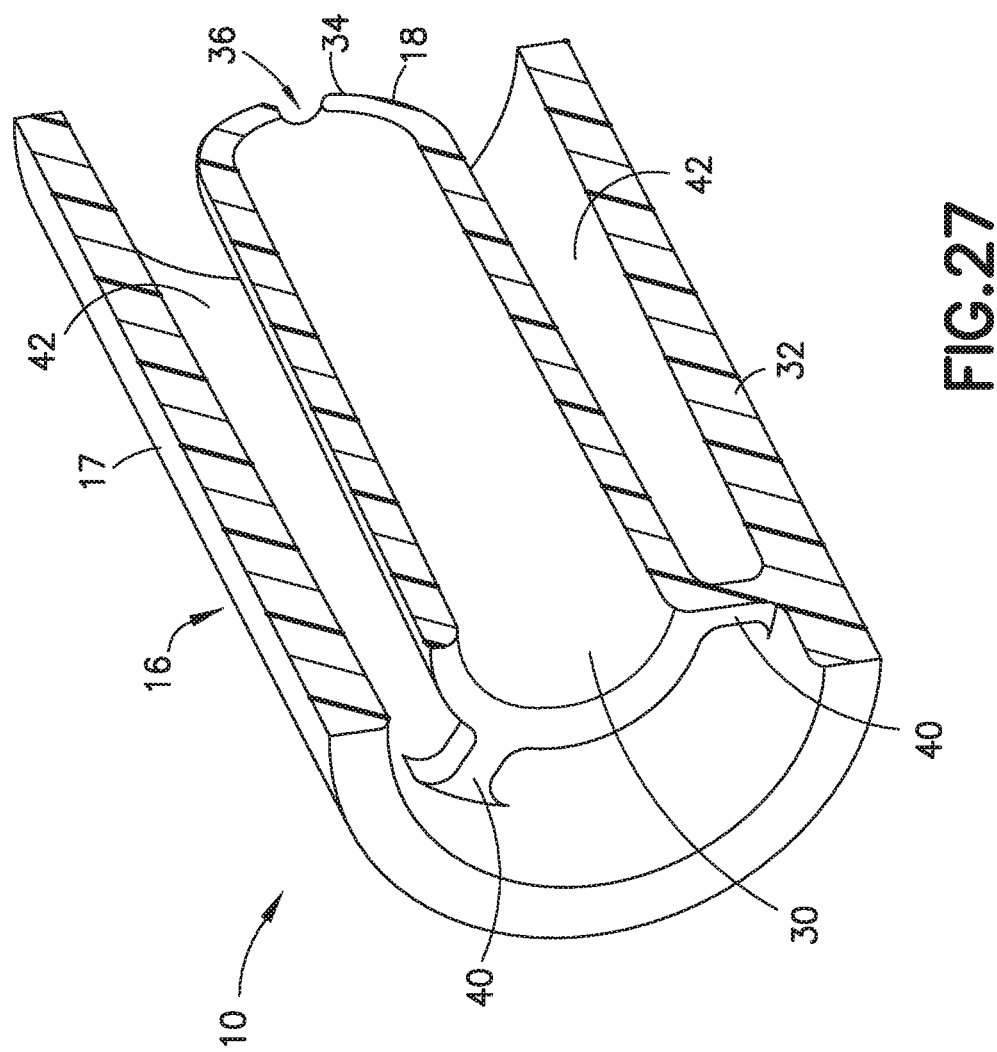

FIG. 27 is a partial perspective cross-sectional view of a biological fluid collection device with a mixer in accordance with an embodiment of the present invention.

FIG. 28 is a partial perspective cross-sectional view of a biological fluid collection device with a mixer and a side exit aperture in accordance with an embodiment of the present invention.

FIG. 29 is a partial perspective cross-sectional view of a biological fluid collection device with a mixer and fins in accordance with an embodiment of the present invention.

FIG. 30 is a front elevation view of a biological fluid collection device with a mixer in accordance with an embodiment of the present invention.

FIG. 31 is a front elevation view of a biological fluid collection device with a mixer and fins in accordance with an embodiment of the present invention.

Figure 32:
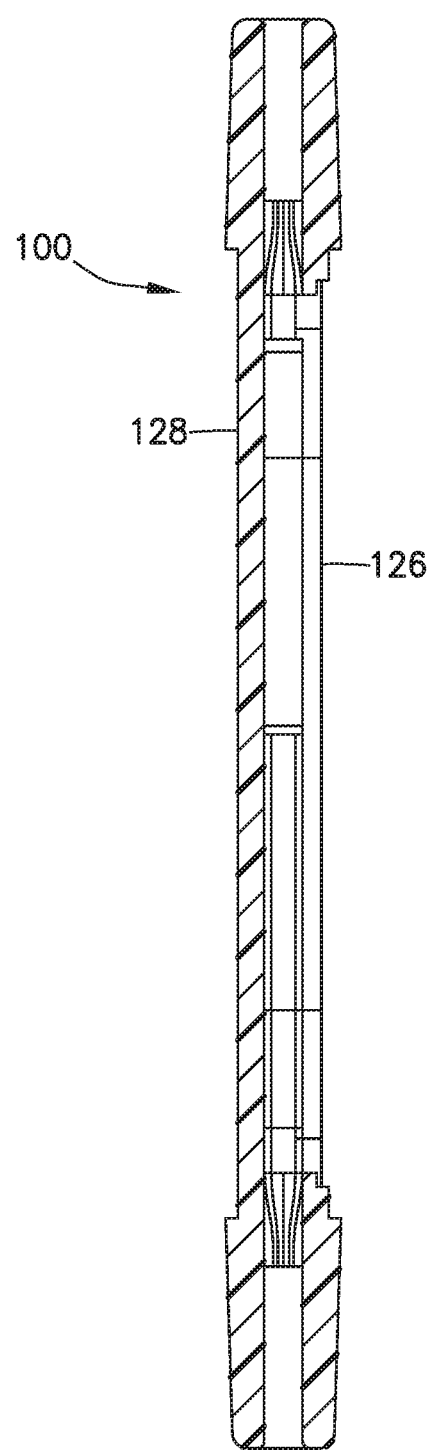

FIG. 32 is a side elevation view of a biological fluid collection device with a mixer in accordance with another embodiment of the present invention.

Figure 33:
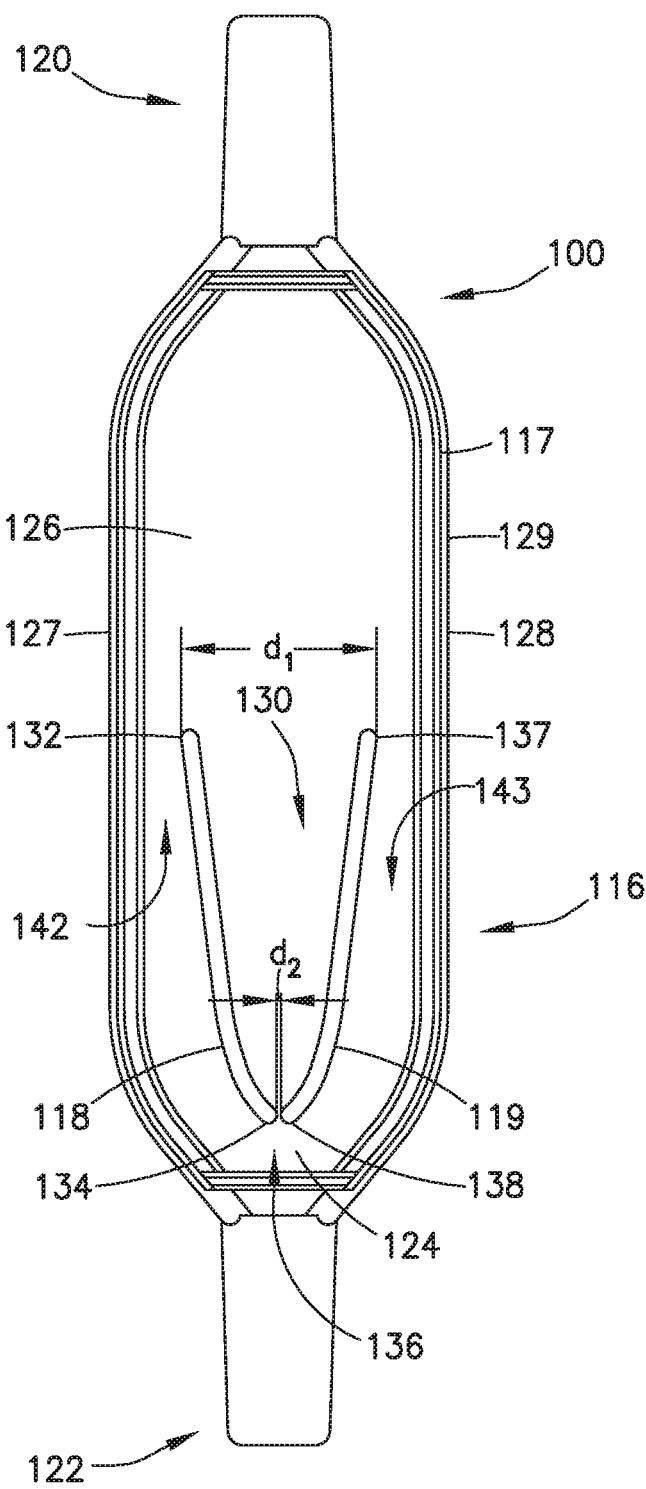

FIG. 33 is a top elevation view of a biological fluid collection device with a mixer in accordance with another embodiment of the present invention.

Figure 34:
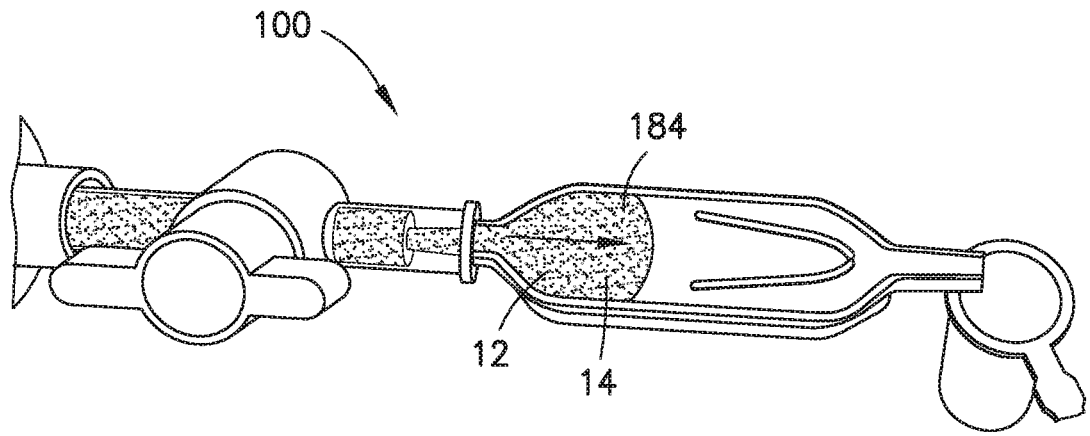

FIG. 34 is a perspective view of a biological fluid collection device illustrating a first step of using a mixer of the present disclosure in accordance with another embodiment of the present invention.

Figure 35:
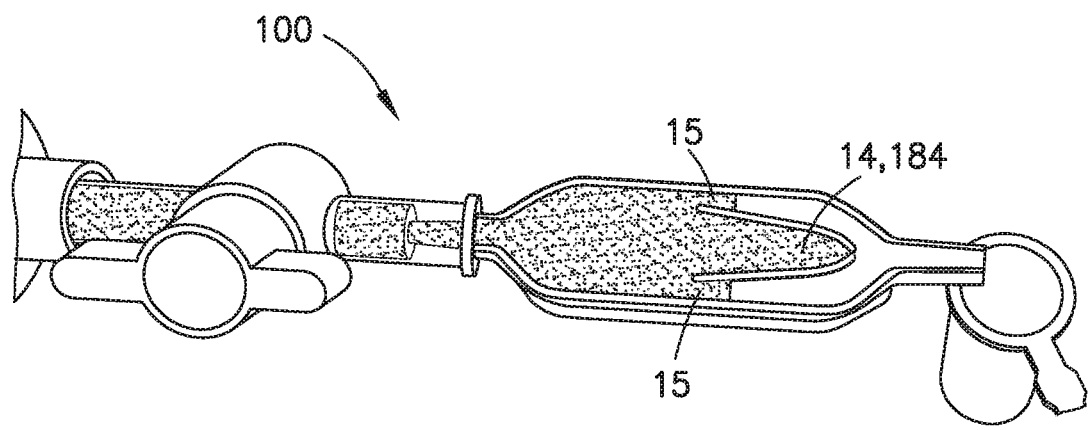

FIG. 35 is a perspective view of a biological fluid collection device illustrating a second step of using a mixer of the present disclosure in accordance with another embodiment of the present invention.

Figure 36:
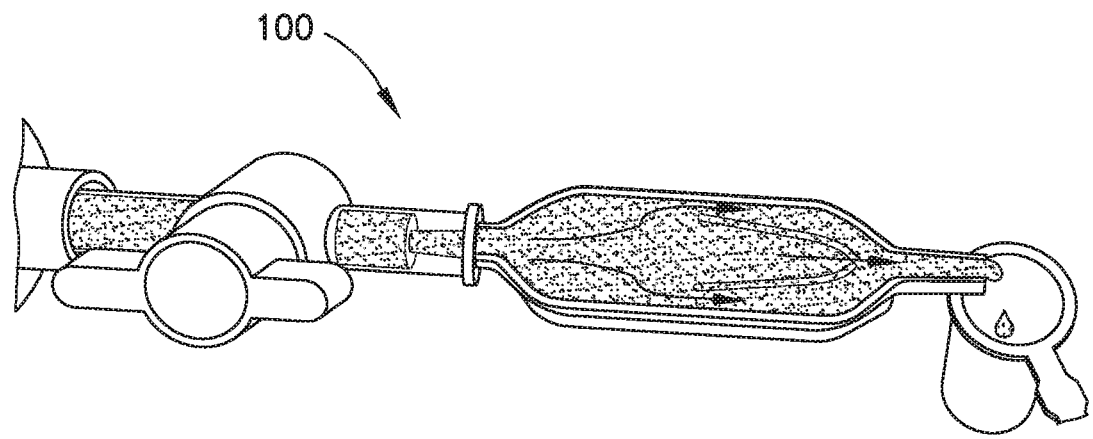

FIG. 36 is a perspective view of a biological fluid collection device illustrating a third step of using a mixer of the present disclosure in accordance with another embodiment of the present invention.

Figure 37:
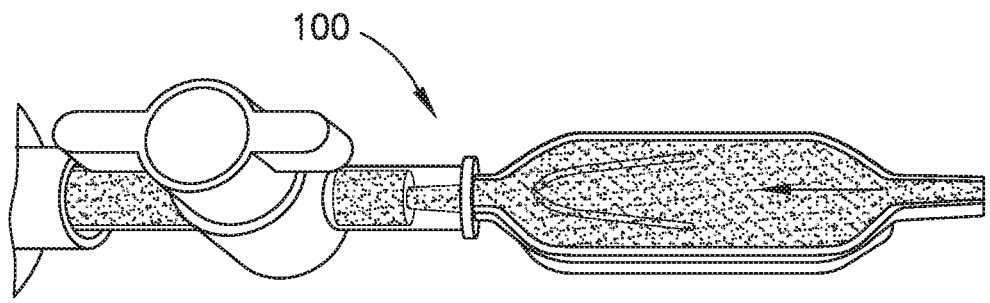

FIG. 37 is a perspective view of a biological fluid collection device illustrating a fourth step of using a mixer of the present disclosure in accordance with another embodiment of the present invention.

Figure 38:
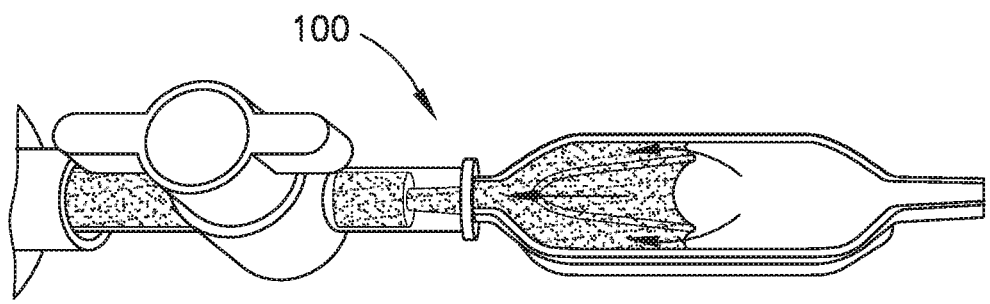

FIG. 38 is a perspective view of a biological fluid collection device illustrating a fifth step of using a mixer of the present disclosure in accordance with another embodiment of the present invention.

Figure 39:
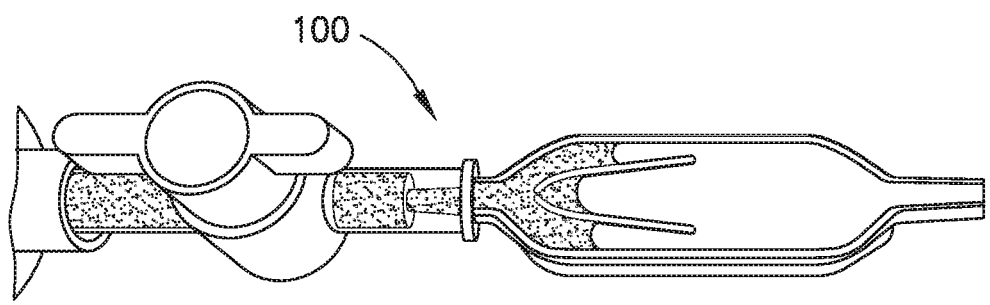

FIG. 39 is a perspective view of a biological fluid collection device illustrating a sixth step of using a mixer of the present disclosure in accordance with another embodiment of the present invention.

Figure 40:
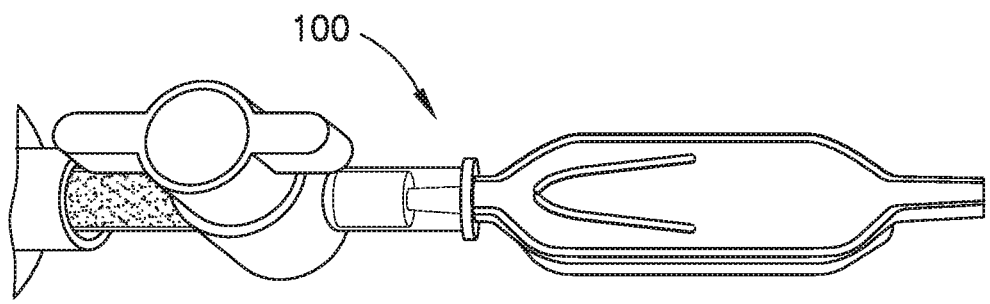

FIG. 40 is a perspective view of a biological fluid collection device illustrating a seventh step of using a mixer of the present disclosure in accordance with another embodiment of the present invention.

FIG. 41 is a partial cross-sectional view of a biological fluid collection device with a mixer in accordance with an embodiment of the present invention.

FIG. 42 is a partial cross-sectional view of a biological fluid collection device with a mixer in accordance with an embodiment of the present invention.

FIG. 43 is a partial cross-sectional view of a biological fluid collection device with a mixer in accordance with an embodiment of the present invention.

FIG. 44 is a partial cross-sectional view of a biological fluid collection device with a mixer in accordance with an embodiment of the present invention.

Figures 45, 46:
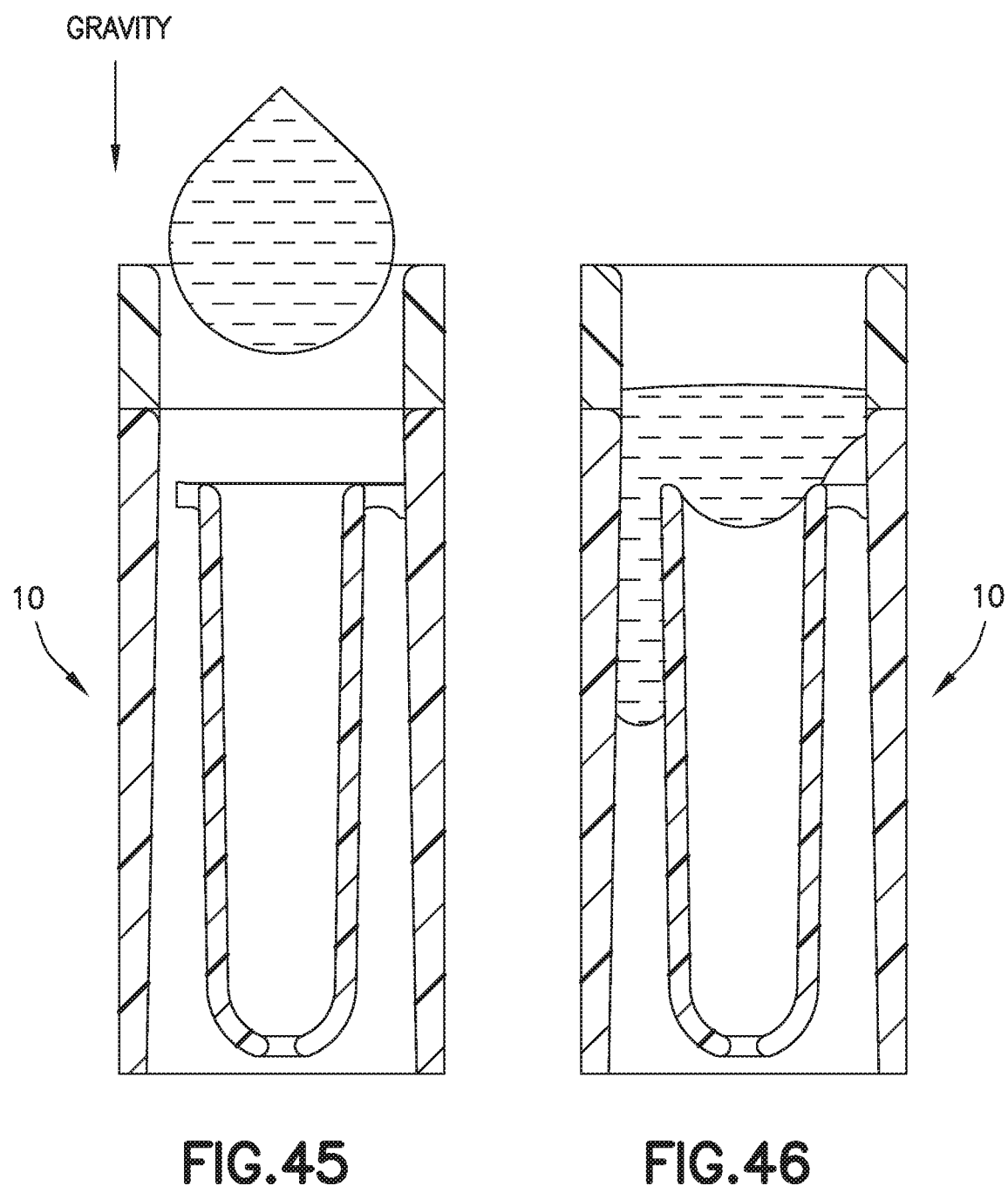

FIG. 45 is a partial cross-sectional view of a biological fluid collection device with a mixer in accordance with an embodiment of the present invention.

FIG. 46 is a partial cross-sectional view of a biological fluid collection device with a mixer in accordance with an embodiment of the present invention.

Figure 47:
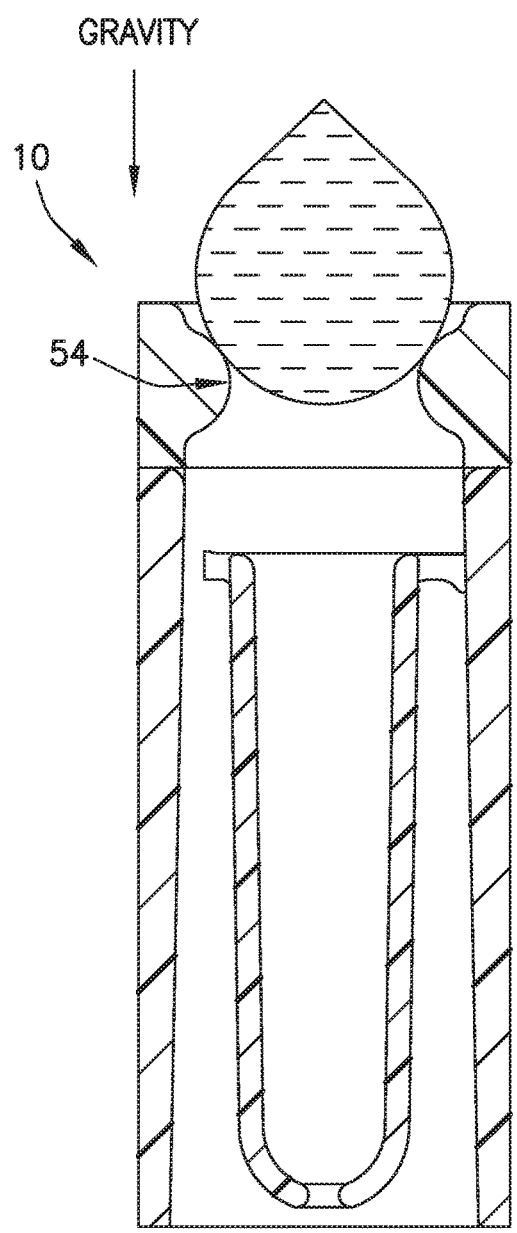

FIG. 47 is a partial cross-sectional view of a biological fluid collection device with a mixer and a pinched entrance in accordance with an embodiment of the present invention.

Figure 48:
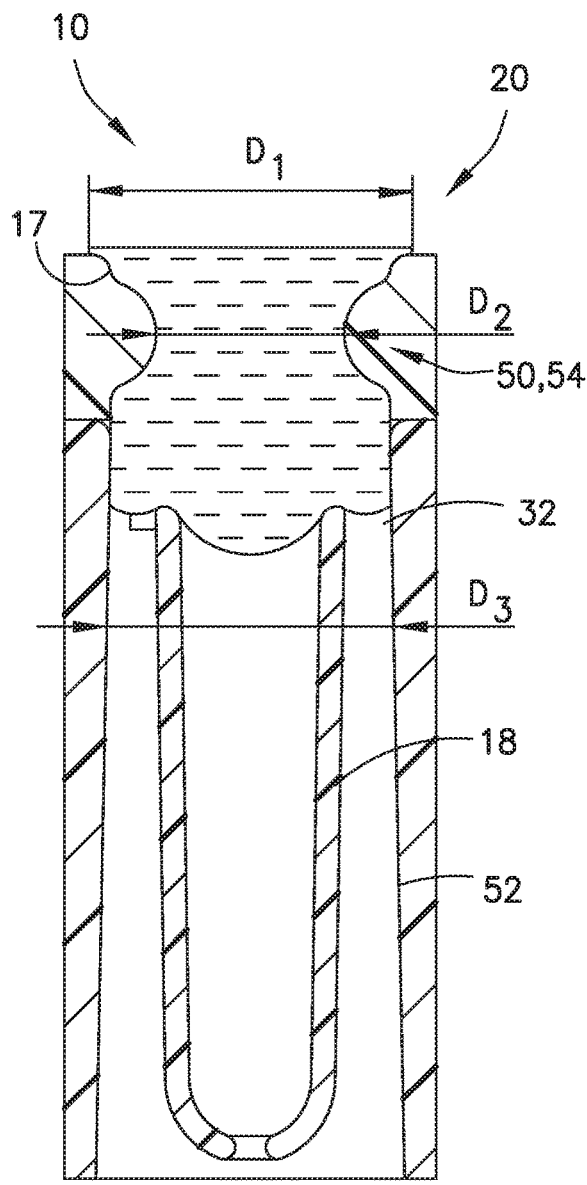

FIG. 48 is a partial cross-sectional view of a biological fluid collection device with a mixer and a pinched entrance in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Referring to FIGS. 1A, 1B, 10, 11, 14, and 15, in conventional devices 500, blood 502 mixing with an anticoagulant 504 in a line will dissolve and push a higher concentration of anticoagulant 504 at its flow front 506 relative to the rest of the flow volume. For example, anticoagulants or additives 504 are often deposited within flow paths of a device or structure 500 to be delivered to a flowing liquid such as blood 502. When dealing with these devices 500, small volumes (<1 mL) and slow flow rates create a dependence on capillary forces and laminar flow conditions. This leads to the additive 504 being dissolved and pushed in front of the flow therefore creating a concentrated flow front 506. Disadvantageously, if the flow volume then needs to be dispensed in the form of discrete drops, it would typically result in the first drop 508 having the largest additive concentration and the last drop 510 having the lowest or no additive concentration as shown in FIGS. 1B, 11, 14, and 15. This behavior is particularly detrimental in terms of whole blood anticoagulation where this concentration gradient promotes rapid clot formation at the tail end of the fluid.

FIGS. 2-9, 12, 13, and 16-48 illustrate exemplary embodiments of a biological fluid collection device of the present disclosure. The present disclosure provides a biological fluid collection device that produces a stabilized biological sample with head-to-tail uniformity through the capturing of a high concentration front and subsequent redistribution of the high concentration front throughout a biological fluid. The biological fluid collection device includes an inline mixer used for head-to-tail mixing of a concentrated flow front. The mixing is achieved via a two-stage process. Referring to FIGS. 2-4B, first, a front fraction of the flow is captured within a centered mixer chamber via capillary assisted flow action. This front fraction consists primarily of the concentrated flow front, e.g., a flow head with a high concentration of anticoagulant. Second, the captured front volume is then slowly released throughout a small exit aperture and recombined with the rest of the flow volume that was diverted around the centered mixer chamber, i.e., a flow tail. This flow recombination improves head-to-tail homogeneity of a selected flow volume, i.e., Control Volume, especially when that volume needs to be further dispensed in the form of discrete drops. A properly mixed head-to-tail control volume would result in significantly improved homogeneity, e.g., anticoagulant concentration, between dispensed discrete drops. Referring to FIGS. 18-25, the mixer of the present disclosure can function properly downstream of many common delivery systems, in both annular and flat designs.

The present disclosure provides a passive inline head-to-tail mixing of a concentrated flow front resulting in uniform redistribution of the additive between dispensed discrete drops. A mixer of the present disclosure redistributes the concentrated front throughout the trailing flow volume, allowing proper anticoagulation of the entire whole blood control volume. This is particularly advantageous in small blood volumes (<1 mL) where traditional bulk mixing techniques could be ineffective.

FIGS. 2-9, 12, 13, 16, 17, and 26-31 illustrate an exemplary embodiment of a biological fluid collection device of the present disclosure. In one embodiment, a biological fluid collection device 10 is adapted to receive a biological fluid, such as a blood sample 12, and includes a sample stabilizer 14 and a mixer or mixing structure 16. In one embodiment, the mixing structure 16 includes an outer wall 17 and an inner wall 18. The present disclosure provides a biological fluid collection device 10 that produces a stabilized biological sample with head-to-tail uniformity through the capturing of a high concentration front and subsequent redistribution of the high concentration front throughout a biological fluid, such as a blood sample 12.

The biological fluid collection device 10 provides an additive, e.g., a sample stabilizer 14, in a concentrated liquid, dry, or solid state which is mixed into a biological fluid, e.g., a blood sample 12, to produce the stabilized biological sample. In one embodiment, the biological fluid collection device 10 includes an inline mixer 16 used for head-to-tail mixing of a concentrated flow front. The mixing is achieved via a two-stage process. First, the biological fluid collection device 10 dissolves the sample stabilizer 14 into a portion of the blood sample 12, e.g., a first or front portion 13 of the blood sample 12. The front portion 13 of the blood sample 12 with the sample stabilizer 14 is captured within a centered mixing chamber via capillary assisted flow action. Second, the captured front volume is then slowly released throughout a small exit aperture at a controlled rate and recombined with the rest of the flow volume, e.g., a second or rear portion 15 of the blood sample 12, which was diverted around the centered mixer chamber.

Referring to FIGS. 2-7, the biological fluid collection device 10 includes a sample stabilizer 14, a mixer or mixing structure 16, an inlet portion 20, an outlet portion 22, and a mixing portion 24. In one embodiment, the mixing structure 16 includes an outer wall 17 and an inner wall 18.

Referring to FIGS. 2-7, the outer wall 17 spans the inlet portion 20 and the outlet portion 22. In one embodiment, the outer wall 17 comprises a cylindrical or annular design. In one embodiment, the outer wall 17 has a constant diameter from the inlet portion 20 to the outlet portion 22. In another embodiment, the outer wall 17 may have portions with different diameters. For example, in one embodiment, referring to FIGS. 47 and 48, the outer wall 17 at the inlet portion 20 has a first diameter D1, and a first portion 50 of the outer wall 17 between the inlet portion 20 and the first end 32 of the inner wall 18 has a second diameter D2. In one embodiment, the second diameter D2 is less than the first diameter D1. In one embodiment, a second portion 52 of the outer wall 17 that is adjacent the inner wall 18 has a third diameter D3. In one embodiment, the third diameter D3 is greater than the second diameter D2. In this manner, a pinched entrance 54 is formed in the biological fluid collection device 10 as shown in FIGS. 47 and 48. The pinched entrance 54 prevents air pockets from being formed during gravity aided drop formation and provides a uniform interface for the capillary filling.

Figure 6:
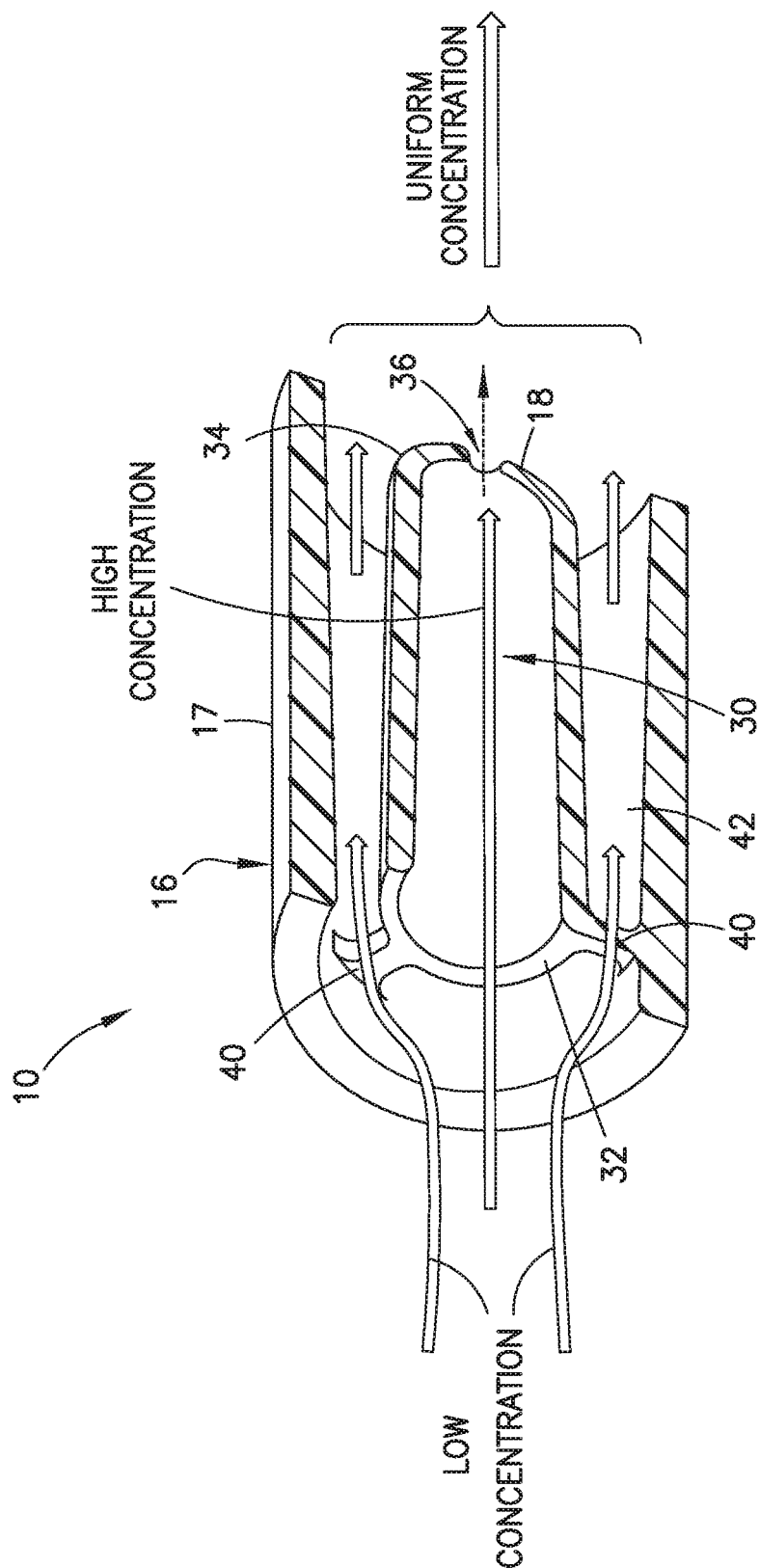
FIG. 6 is a partial perspective cross-sectional view of a biological fluid collection device with a mixer in accordance with an embodiment of the present invention.
Figure 8:
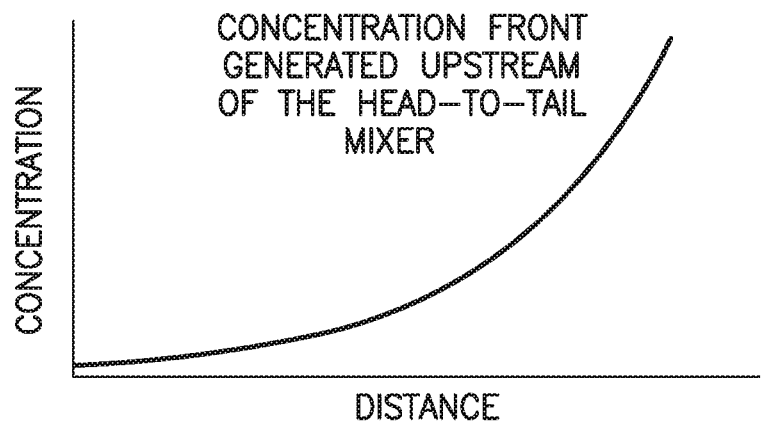
FIG. 8 is a graph of a concentration front generated upstream of a head-to-tail mixer in accordance with an embodiment of the present invention.
Figure 9:
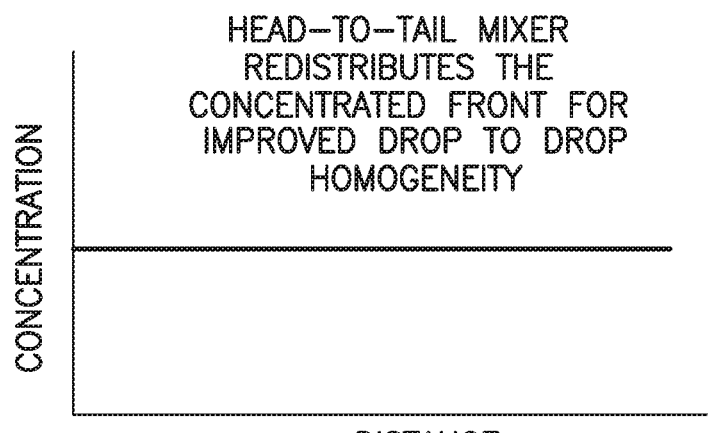
FIG. 9 is a graph of a head-to-tail mixer of the present disclosure that redistributes the concentrated front for improved drop to drop homogeneity in accordance with an embodiment of the present invention.
Figure 10:
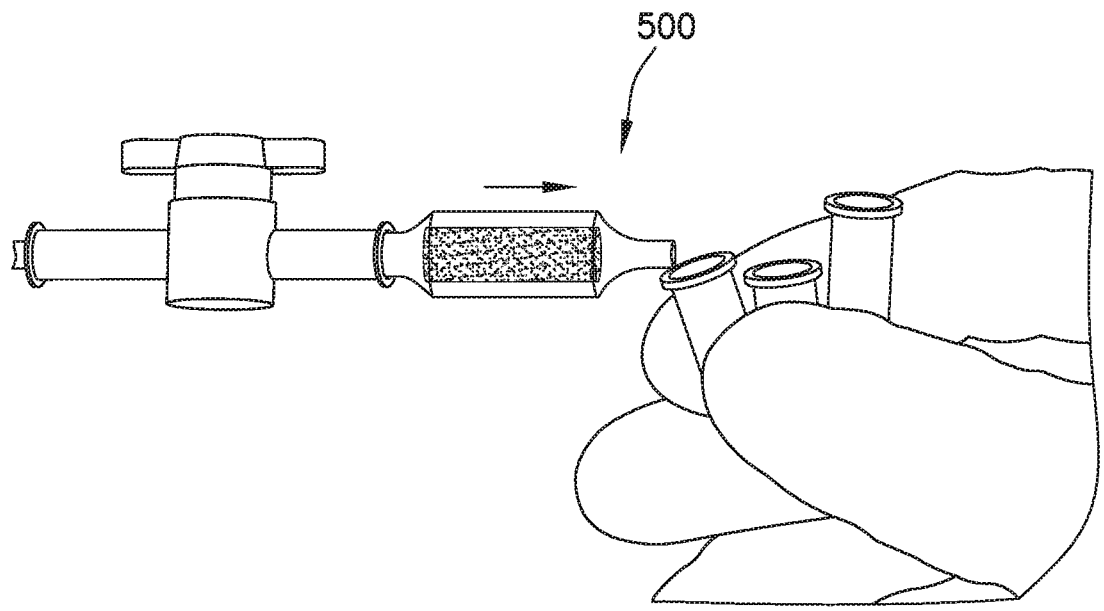
Figure 11:
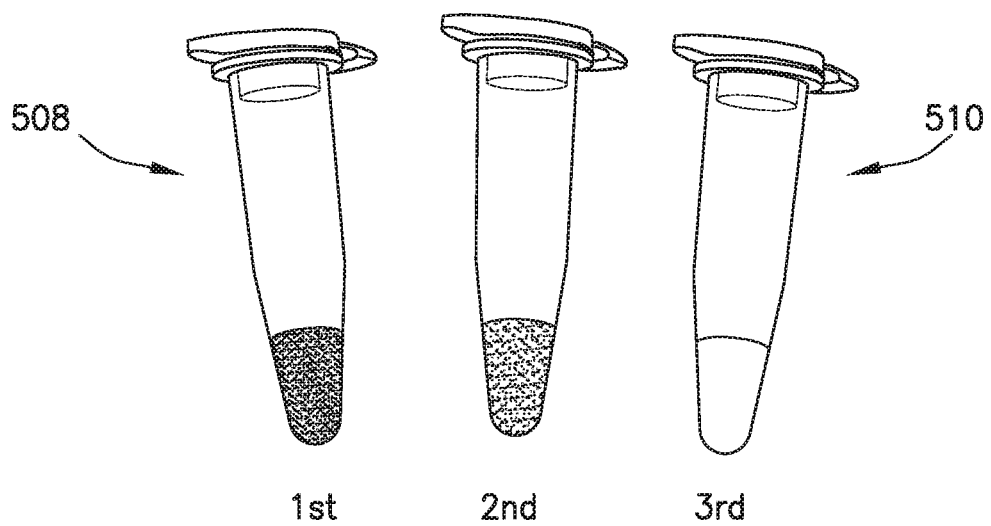
Figure 12:
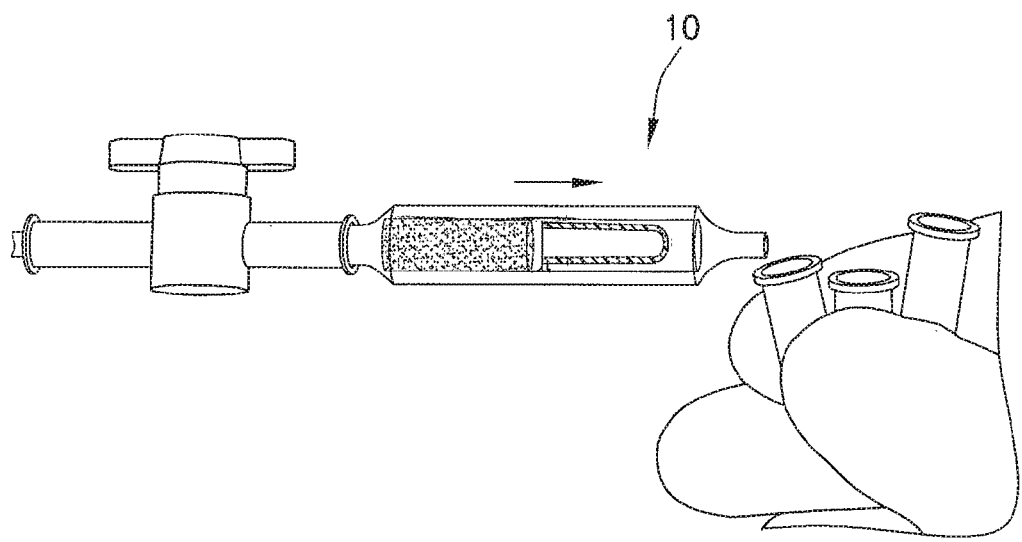

Referring to FIGS. 2-7, the inner wall 18 is disposed within the interior of the outer wall 17 and is spaced from the outer wall 17 as shown in FIG. 6. In one embodiment, the inner wall 18 defines a chamber 30 therein and includes a first end 32 and a second end 34. The first end 32 of the inner wall 18 is in fluid communication with the inlet portion 20 and the second end 34 of the inner wall 18 defines an exit aperture 36.

The exit aperture 36 located at the second end 34 of the centered chamber 30 promotes uniform distribution of dissolved additive by facilitating the slow release of the captured front to the remaining control volume that has been diverted around the centered chamber 30. Redistribution and head-to-tail mixing can be accomplished by varying exit hole diameter/count/location, incorporating fins to promote rotational mixing, and changing the center chamber volume to handle larger control volumes.

In one embodiment, the first end 32 is open and defines a first cross-sectional area. In one embodiment, the inner wall 18 is secured to the outer wall 17 via a connection portion 40. For example, a plurality of connection portions 40 may connect the inner wall 18 and the outer wall 17 as shown in FIG. 6.

In one embodiment, a flow channel 42 is disposed between the outer wall 17 and the inner wall 18. The flow channel 42 in fluid communication with the inlet portion 20. The flow channel 42 defines a separate flow path from a flow path defined by the chamber 30 of the inner wall 18. In one embodiment, a distance between the inner wall 18 and the outer wall 17, e.g., the diameter of the flow channel 42, is greater than a diameter of the exit aperture 36.

In one embodiment, the outer wall 17 of the biological fluid collection device 10 includes a mixing portion 24 that is disposed between the second end 34 of the inner wall 18 and the outlet portion 22. In this manner, a portion of the flow channel 42 and a portion of the chamber 30 are each in fluid communication with the mixing portion 24.

In one embodiment, a sample stabilizer 14 is disposed within an interior of the outer wall 17. In one embodiment, the sample stabilizer 14 is disposed within an interior of the outer wall 17 between the inlet portion 20 and the first end 32 of the inner wall 18.

The biological fluid collection device 10 provides an additive and/or sample stabilizer 14 in a concentrated liquid or solid state. The biological fluid collection device 10 produces a stabilized biological sample with head-to-tail uniformity through the capturing of a high concentration front and subsequent redistribution of the high concentration front throughout a biological fluid. The sample stabilizer 14 can be an anticoagulant, or a substance designed to preserve a specific element within the blood such as, for example, RNA, protein analyte, or other element. In one embodiment, the sample stabilizer 14 is heparin or EDTA. In one embodiment, a plurality of biological fluid collection devices 10 could include different sample stabilizers. A biological fluid collection device 10 of the present disclosure provides flexibility in the nature of the additives and/or sample stabilizers introduced for a blood sample. In one embodiment, a blood sample received within a biological fluid collection device of the present disclosure may be divided into separate portions and different sample stabilizers may be added to the separate portions of the blood sample. In this manner, a biological fluid collection device of the present disclosure can stabilize multiple portions of a blood sample with different sample stabilizers within a single device.

In one embodiment, a sample stabilizer 14 is disposed within a portion of the outer wall 17. For example, a sample stabilizer 14 such as dry additives, reagents, or anticoagulants c a n b e deposited within flow paths of a biological fluid collection devices 10 to be delivered to a flowing liquid such as a blood sample 12. Referring to FIGS. 18-25, some examples of these include capillary tubes 60 (FIG. 18), porous media 62 (FIG. 19), beads 64 (FIG. 20), or three dimensional microfluidic structures 66 (FIGS. 21-25).

Referring to FIG. 19, the biological fluid collection devices 10 includes a material 70 including pores 72 and disposed within the interior of the outer wall 17, and the sample stabilizer 14 comprises a dry anticoagulant powder 74 within the pores 72 of the material 70.

In one embodiment, the material 70 is a sponge material. In other embodiments, the material 70 is an open cell foam. In one embodiment, the open cell foam is treated with an anticoagulant, as described in detail below, to form a dry anticoagulant powder 74 finely distributed throughout the pores 72 of the material 70. A blood sample 12 may be received within the biological fluid collection devices 10. In some embodiments, the blood sample 12 gets soaked into the material 70 based on capillary principles. The blood sample 12 is exposed to and mixes with the anticoagulant powder 74 while passing through the intricate microstructure of the material 70.

In one embodiment, the material 70 is an open cell foam. For example, the material 70 is a soft deformable open cell foam that is inert to blood. In one embodiment, the open cell foam may be a melamine foam, such as Basotect® foam commercially available from BASF. In another embodiment, the open cell foam may consist of a formaldehyde-melamine-sodium bisulfite copolymer. The open cell foam may be a flexible, hydrophilic open cell foam that is resistant to heat and many organic solvents. In one embodiment, the open cell foam may be a sponge material.

A method of loading an anticoagulant to a material 70 having pores 72 will now be discussed. In one embodiment, the method includes soaking the material 70 in a liquid solution of the anticoagulant and water; evaporating the water of the liquid solution; and forming a dry anticoagulant powder 74 within the pores 72 of the material 70.

The method of the present disclosure enables precisely controlled loading of an anticoagulant into the material 70 by soaking it with an anticoagulant and water solution and then drying the material 70 to form a finely distributed dry anticoagulant powder 74 throughout the pores 72 of the material 70.

Anticoagulants such as Heparin or EDTA (Ethylene Diamine Tetra Acetic Acid), as well as other blood stabilization agents, could be introduced into the material 70 as a liquid solution by soaking the material 70 in the liquid solution of a desired concentration. After evaporating the liquid phase, e.g., evaporating the water from a water and Heparin solution, a dry anticoagulant powder 74 is formed and finely distributed throughout the internal structure of the material 70. For example, the dry anticoagulant powder 74 is formed and finely distributed throughout the pores 72 of the material 70. In a similar manner, the material 70 could be treated to provide a hydrophobic, hydrophilic, or reactive internal pore surface.

In one configuration, a key advantage of providing an open cell foam as the material 70 is that a known amount of anticoagulant may be loaded into the pores 72 of the foam material. A desired concentration of an anticoagulant may be dissolved in water or other suitable solvent and then introduced into the pores 72 of the open cell foam material 70 in liquid form. In one embodiment, the anticoagulant may be loaded into the pores 72 by dipping the open cell foam material 70 into a solution of anticoagulant and water or solvent and subsequently allowing the open cell foam material 70 to dry. The open cell foam material 70 may be allowed to dry in ambient air or in a heated oven. After drying, the anticoagulant may be distributed throughout the internal microstructure of the open cell foam material 70 in the form of a dry powder.

In one embodiment, referring to FIG. 18, the sample stabilizer 14 comprises a dry anticoagulant powder 68 disposed within the interior of the outer wall 17. For example, the tube 60 may be coated with a dry anticoagulant powder 68.

Referring to FIGS. 21-25, a three dimensional microfluidic structure 66 may include any configuration of pores 69, including different cross-sectional geometric shapes as shown in FIGS. 22-25.

Referring to FIGS. 29 and 31, in one embodiment, the biological fluid collection device 10 includes fins 80 to promote rotational mixing. Referring to FIG. 28, in one embodiment, the biological fluid collection device 10 includes an inner wall 18 that defines a side exit aperture 82.

Referring to FIGS. 2-7, use of a biological fluid collection device 10 of the present disclosure will now be described. The inlet portion 20 of the biological fluid collection device 10 is adapted to receive a blood sample 12 therein. As discussed above, a sample stabilizer 14 is disposed within a portion of the outer wall 17. In one embodiment, the sample stabilizer 14 is disposed within a portion of the outer wall 17 between the inlet portion 20 and the first end 32 of the inner wall 18.

With the blood sample 12 received within the inlet portion 20 of the biological fluid collection device 10, the sample stabilizer 14 mixes with the blood sample 12. With the blood sample 12 mixing with the sample stabilizer 14, a first additive front 84 is created within a front portion 13 of the blood sample 12.

Figure 1A:
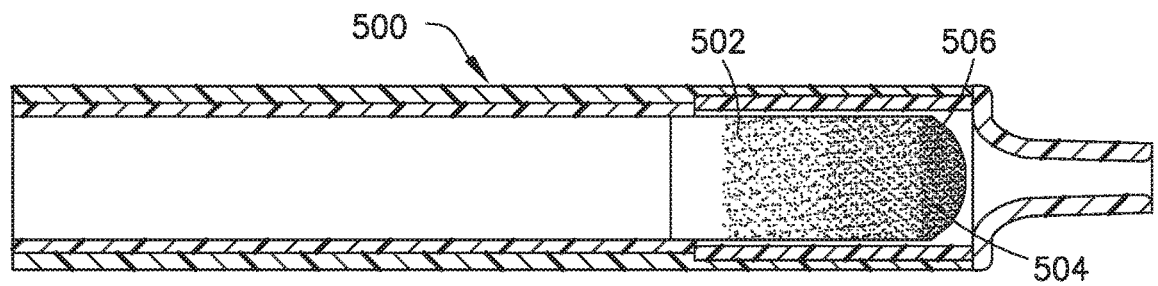
FIG. 1A is a partial cross-sectional view of a conventional biological fluid collection device.
Figure 1B:
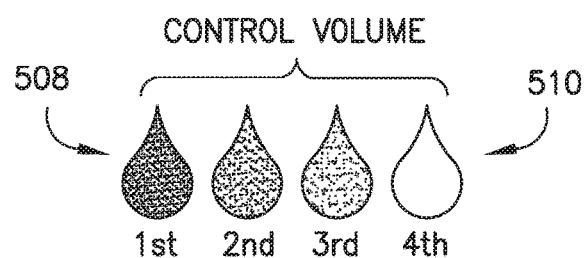
FIG. 1B is a perspective view of a drop to drop concentration yielded by a conventional biological fluid collection device.
Figure 2:
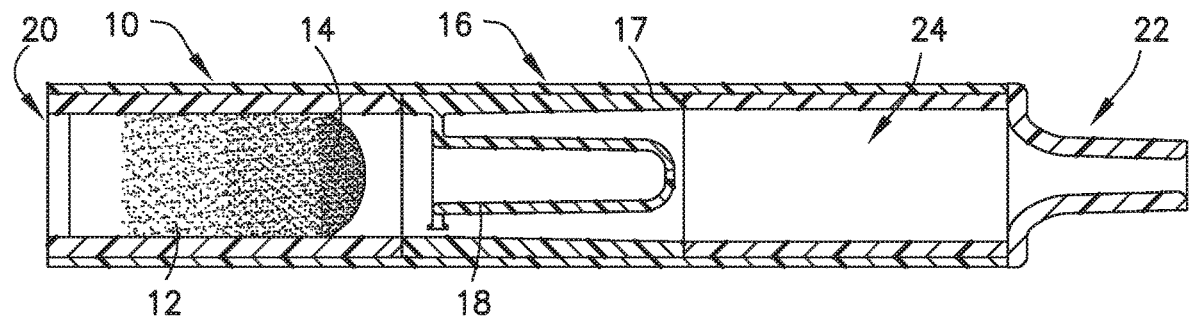
FIG. 2 is a partial cross-sectional view of a biological fluid collection device illustrating a first step of using a mixer of the present disclosure in accordance with an embodiment of the present invention.
Figure 3:
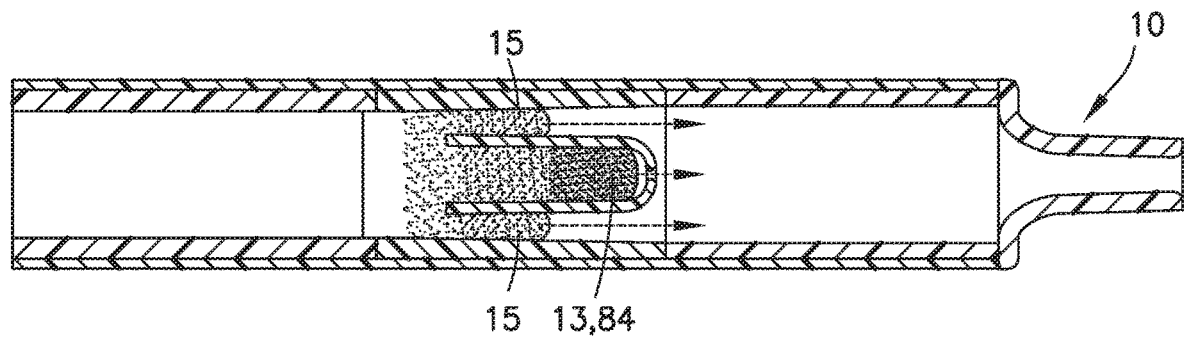
FIG. 3 is a partial cross-sectional view of a biological fluid collection device illustrating a second step of using a mixer of the present disclosure in accordance with an embodiment of the present invention.
Figure 4B:
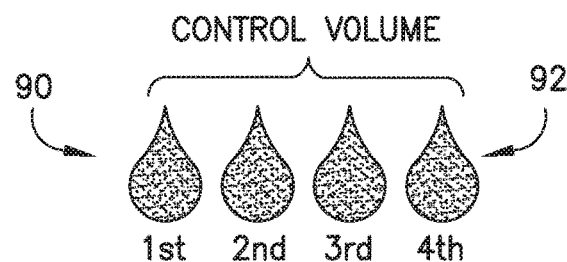
FIG. 4B is a perspective view of a drop to drop concentration yielded by a biological fluid collection device with a mixer in accordance with an embodiment of the present invention.
Figure 4A:
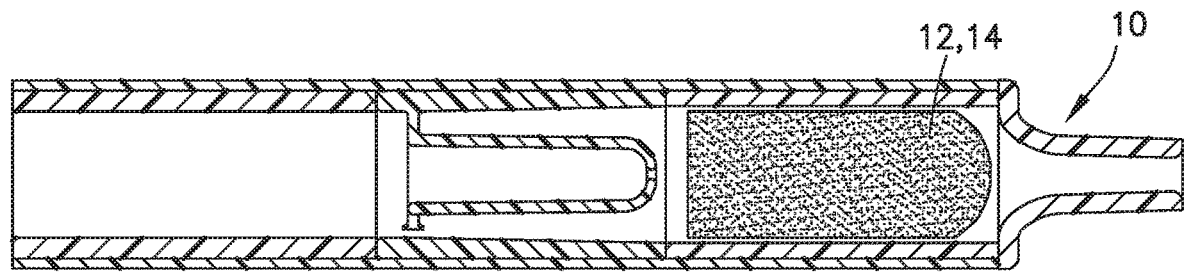
FIG. 4A is a partial cross-sectional view of a biological fluid collection device illustrating a third step of using a mixer of the present disclosure in accordance with an embodiment of the present invention.

Next, referring to FIG. 3, the front portion 13 of the blood sample 12 containing the additive front 84 flows into the chamber 30 of the inner wall 18 and a rear portion 15 of the blood sample 12 flows into the flow channel 42 disposed between the outer wall 17 and the inner wall 18. The front portion 13 of the blood sample 12 flows through the chamber 30 to the exit aperture 36 and the rear portion 15 of the blood sample 12 flows through the flow channel 42 to the mixing portion 24 of the biological fluid collection device 10. Next, the front portion 13 of the blood sample 12 with the first additive front 84 flows through the exit aperture 36 to the mixing portion 24 at a controlled rate back into the rear portion 15 of the blood sample 12.

The front portion 13 of the blood sample 12 with the first additive front 84 flows through the exit aperture 36 to the mixing portion 24 back into the rear portion 15 of the blood sample 12 to effectuate metered mixing of the sample stabilizer 14 within the front portion 13 of the blood sample 12 and the rear portion 15 of the blood sample 12. In this manner, the biological fluid collection device 10 produces a stabilized biological sample with head-to-tail uniformity through the capturing of a high concentration front, e.g., the first additive front 84, and subsequent redistribution of the high concentration front throughout a biological fluid. The biological fluid collection device includes an inline mixer, e.g., mixing structure 16, used for head-to-tail mixing of a concentrated flow front. The mixing is achieved via a two-stage process. Referring to FIGS. 2-4B, first, a front fraction of the flow, e.g., a front portion 13 of the blood sample 12, is captured within a centered mixer chamber 30 of the inner wall 18 via capillary assisted flow action. This front fraction consists primarily of the concentrated flow front, e.g., a flow head with a high concentration of anticoagulant. Second, the captured front volume is then slowly released throughout a small exit aperture 36 and recombined with the rest of the flow volume that was diverted around the centered mixer chamber, i.e., a flow tail or the rear portion 15 of the blood sample 12. This flow recombination improves head-to-tail homogeneity of a selected flow volume, i.e., Control Volume, especially when that volume needs to be further dispensed in the form of discrete drops. A properly mixed head-to-tail control volume would result in significantly improved homogeneity, e.g., anticoagulant concentration, between dispensed discrete drops. For example, referring to FIGS. 4B, 7, 9, 13, 16, and 17, a stabilized biological sample with head-to-tail uniformity of a sample stabilizer is produced with a biological fluid collection device 10 of the present disclosure. Advantageously, if the flow volume then needs to be dispensed in the form of discrete drops, a biological fluid collection device 10 of the present disclosure results in a first drop 90 and a last drop 92 having improved drop to drop homogeneity as shown in FIGS. 4B, 7, 9, 13, and 17.

In one embodiment, the size or diameter of the exit aperture 36 controls the resistance of the flow of the front portion 13 of the blood sample 12 with the additive front 84 back into the rear portion 15 of the blood sample 12. For example, in one embodiment, a distance between the inner wall 18 and the outer wall 17, e.g., the diameter of the flow channel 42, is greater than a diameter of the exit aperture 36. In this manner, there is a lower resistance through the exit of the flow channel 42 than at the exit aperture 36 so that the front portion 13 of the blood sample 12 with the first additive front 84 flows through the exit aperture 36 to the mixing portion 24 at a controlled rate back into the rear portion 15 of the blood sample 12.

The biological fluid collection device 10 meters the front portion 13 of the blood sample 12 with the additive front 84 back into the rear portion 15 of the blood sample 12 to achieve a single flow stream, i.e., the stabilized biological sample, with the sample stabilizer 14 distributed along the single flow stream.

After a stabilized biological sample with head-to-tail uniformity is produced by the biological fluid collection device 10, the stabilized biological sample flows to the outlet portion 22. At this time, the biological fluid collection device 10 may be engaged with a blood testing device or point-of-care testing device for closed transfer of a portion of the stabilized biological sample from the biological fluid collection device 10 to the blood testing device or point-of-care testing device. The blood testing device is adapted to receive the stabilized biological sample to analyze the stabilized biological sample and obtain test results.

A biological fluid collection device 10 of the present disclosure rapidly captures and redistributes a concentrated flow front throughout the lower concentration flow tail. This is of particular interest because many prior art devices have problems uniformly distributing dry additive in small sample volumes. At these volumes, a biological fluid collection device 10 of the present disclosure takes advantage of capillary forces to preferentially fill the mixer's center chamber (volume=<10-1000 μL).

In one embodiment, referring to FIGS. 41 and 42, when the front portion 13 of the blood sample 12 reaches the front of the mixer 16, the hydrophobic contact angle between the fluid and material results in preferential filling of the center chamber 30. This captures the concentrated front in the center chamber 30. The hole or exit aperture 36 located at the exit end 34 of the centered chamber 30 promotes uniform distribution of dissolved additive by facilitating the slow release of the captured front to the remaining control volume that has been diverted around the centered chamber 30. Redistribution and head-to-tail mixing can be accomplished by varying exit hole diameter/count/location, incorporating fins to promote rotational mixing, and changing the center chamber volume to handle larger control volumes.

FIGS. 32-40 illustrate another exemplary embodiment of a biological fluid collection device of the present disclosure. In one embodiment, a biological fluid collection device 100 is adapted to receive a biological fluid, such as a blood sample 12, and includes a sample stabilizer 14 and a mixer or mixing structure 116. In one embodiment, the mixing structure 116 includes an outer wall 117, a first inner wall 118, and a second inner wall 119. The present disclosure provides a biological fluid collection device 100 that produces a stabilized biological sample with head-to-tail uniformity through the capturing of a high concentration front and subsequent redistribution of the high concentration front throughout a biological fluid, such as a blood sample 12.

The biological fluid collection device 100 provides an additive, e.g., a sample stabilizer 14, in a concentrated liquid, dry, or solid state which is mixed into a biological fluid, e.g., a blood sample 12, to produce the stabilized biological sample. In one embodiment, the biological fluid collection device 100 includes an inline mixer 116 used for head-to-tail mixing of a concentrated flow front. The mixing is achieved via a two-stage process. First, the biological fluid collection device 100 dissolves the sample stabilizer 14 into a portion of the blood sample 12, e.g., a first or front portion 13 of the blood sample 12. The front portion 13 of the blood sample 12 with the sample stabilizer 14 is captured within a centered mixing chamber via capillary assisted flow action. Second, the captured front volume is then slowly released throughout a small exit aperture at a controlled rate and recombined with the rest of the flow volume, e.g., a second or rear portion 15 of the blood sample 12, which was diverted around the centered mixer chamber.

Referring to FIGS. 32-40, the biological fluid collection device 100 includes a sample stabilizer 14, a mixer or mixing structure 116, an inlet portion 120, an outlet portion 122, and a mixing portion 124. In one embodiment, the mixing structure 116 includes an outer wall 117, a first inner wall 118, and a second inner wall 119.

Referring to FIGS. 32-40, the outer wall 117 spans the inlet portion 120 and the outlet portion 122. In one embodiment, the outer wall 117 includes a top wall 126, a bottom wall 128, a first sidewall 127, and a second sidewall 129.

Referring to FIGS. 32-40, a first inner wall 118 is disposed within the interior of the outer wall 117 and spans the top wall 126 and the bottom wall 128. In one embodiment, the first inner wall 118 includes a first inner wall first end 132 and a first inner wall second end 134. Referring to FIGS. 32-40, a second inner wall 119 is disposed within the interior of the outer wall 117 and spans the top wall 126 and the bottom wall 128. In one embodiment, the second inner wall 119 includes a second inner wall first end 137 and a second inner wall second end 138.

In one embodiment, the first inner wall 118 and the second inner wall 119 together define a chamber 130 therebetween. The chamber 130 is in fluid communication with the inlet portion 120. In one embodiment, the first inner wall first end 132 is spaced a first distance d1 from the second inner wall first end 137 and the first inner wall second end 134 is spaced a second distance d2 from the second inner wall second end 138. In one embodiment, the second distance d2 is less than the first distance d1. In one embodiment, the second distance d2 defines an exit aperture 136.

The exit aperture 136 of the centered chamber 130 promotes uniform distribution of dissolved additive by facilitating the slow release of the captured front to the remaining control volume that has been diverted around the centered chamber 130. Redistribution and head-to-tail mixing can be accomplished by varying exit hole diameter/count/location, incorporating fins to promote rotational mixing, and changing the center chamber volume to handle larger control volumes.

In one embodiment, a first flow channel 142 is disposed between a first portion of the outer wall, e.g., the first sidewall 127, and the first inner wall 118. In one embodiment, the first flow channel 142 is in fluid communication with the inlet portion 120.

In one embodiment, a second flow channel 143 is disposed between a second portion of the outer wall, e.g., the second sidewall 129, and the second inner wall 119. In one embodiment, the second flow channel 143 is in fluid communication with the inlet portion 120.

The flow channels 142, 143 define separate flow paths from a flow path defined by the chamber 130. In one embodiment, the diameter of the flow channels 142, 143 is greater than a diameter of the exit aperture 136.

In one embodiment, the outer wall 117 of the biological fluid collection device 100 includes a mixing portion 124 that is disposed between the first inner wall second end 134 and the outlet portion 122. In this manner, a portion of the flow channels 142, 143 and a portion of the chamber 130 are each in fluid communication with the mixing portion 124.

In one embodiment, a sample stabilizer 14 is disposed within a portion of the outer wall 117. In one embodiment, the sample stabilizer 14 is disposed within a portion of the outer wall 117 between the inlet portion 120 and the first end 132 of the first inner wall 118.

The biological fluid collection device 100 provides an additive and/or sample stabilizer 14 in a concentrated liquid or solid state. The biological fluid collection device 100 produces a stabilized biological sample with head-to-tail uniformity through the capturing of a high concentration front and subsequent redistribution of the high concentration front throughout a biological fluid. The sample stabilizer 14 can be an anticoagulant, or a substance designed to preserve a specific element within the blood such as, for example, RNA, protein analyte, or other element. In one embodiment, the sample stabilizer 14 is heparin or EDTA. In one embodiment, a plurality of biological fluid collection devices 100 could include different sample stabilizers. A biological fluid collection device 100 of the present disclosure provides flexibility in the nature of the additives and/or sample stabilizers introduced for a blood sample. In one embodiment, a blood sample received within a biological fluid collection device of the present disclosure may be divided into separate portions and different sample stabilizers may be added to the separate portions of the blood sample. In this manner, a biological fluid collection device of the present disclosure can stabilize multiple portions of a blood sample with different sample stabilizers within a single device.

In one embodiment, a sample stabilizer 14 is disposed within a portion of the outer wall 117. For example, a sample stabilizer 14 such as dry additives, reagents, or anticoagulants can be deposited within flow paths of a biological fluid collection devices 100 to be delivered to a flowing liquid such as a blood sample 12. As described in detail above, referring to FIGS. 18-25, some examples of these include capillary tubes 60 (FIG. 18), porous media 62 (FIG. 19), beads 64 (FIG. 20), or three dimensional microfluidic structures 66 (FIGS. 21-25).

Referring to FIGS. 32-40, use of a biological fluid collection device 100 of the present disclosure will now be described. The inlet portion 120 of the biological fluid collection device 100 is adapted to receive a blood sample 12 therein. As discussed above, a sample stabilizer 14 is disposed within a portion of the outer wall 117. In one embodiment, the sample stabilizer 14 is disposed within a portion of the outer wall 117 between the inlet portion 120 and the first end 132 of the first inner wall 118.

With the blood sample 12 received within the inlet portion 120 of the biological fluid collection device 100, the sample stabilizer 14 mixes with the blood sample 12. With the blood sample 12 mixing with the sample stabilizer 14, a first additive front 184 is created within a front portion 13 of the blood sample 12.

Next, referring to FIGS. 34-36, the front portion 13 of the blood sample 12 containing the additive front 184 flows into the chamber 130 and a rear portion 15 of the blood sample 12 flows into the flow channels 142, 143. The front portion 13 of the blood sample 12 flows through the chamber 130 to the exit aperture 136 and the rear portion 15 of the blood sample 12 flows through the flow channels 142, 143 to the mixing portion 124 of the biological fluid collection device 100. Next, the front portion 13 of the blood sample 12 with the first additive front 184 flows through the exit aperture 136 to the mixing portion 124 at a controlled rate back into the rear portion 15 of the blood sample 12.

The front portion 13 of the blood sample 12 with the first additive front 184 flows through the exit aperture 136 to the mixing portion 124 back into the rear portion 15 of the blood sample 12 to effectuate metered mixing of the sample stabilizer 14 within the front portion 13 of the blood sample 12 and the rear portion 15 of the blood sample 12. In this manner, the biological fluid collection device 100 produces a stabilized biological sample with head-to-tail uniformity through the capturing of a high concentration front, e.g., the first additive front 184, and subsequent redistribution of the high concentration front throughout a biological fluid. The biological fluid collection device includes an inline mixer, e.g., mixing structure 116, used for head-to-tail mixing of a concentrated flow front. The mixing is achieved via a two-stage process. Referring to FIGS. 32-40, first, a front fraction of the flow, e.g., a front portion 13 of the blood sample 12, is captured within a centered mixer chamber 130 via capillary assisted flow action. This front fraction consists primarily of the concentrated flow front, e.g., a flow head with a high concentration of anticoagulant. Second, the captured front volume is then slowly released throughout a small exit aperture 136 and recombined with the rest of the flow volume that was diverted around the centered mixer chamber, i.e., a flow tail or the rear portion 15 of the blood sample 12. This flow recombination improves head-to-tail homogeneity of a selected flow volume, i.e., Control Volume, especially when that volume needs to be further dispensed in the form of discrete drops. A properly mixed head-to-tail control volume would result in significantly improved homogeneity, e.g., anticoagulant concentration, between dispensed discrete drops. For example, referring to FIGS. 4B, 9, and 13, a stabilized biological sample with head-to-tail uniformity of a sample stabilizer is produced with a biological fluid collection device 100 of the present disclosure.

In one embodiment, the size or diameter of the exit aperture 136 controls the resistance of the flow of the front portion 13 of the blood sample 12 with the additive front 184 back into the rear portion 15 of the blood sample 12. For example, in one embodiment, the diameter of the flow channels 142, 143 is greater than a diameter of the exit aperture 136. In this manner, there is a lower resistance through the exit of the flow channels 142, 143 than at the exit aperture 136 so that the front portion 13 of the blood sample 12 with the first additive front 184 flows through the exit aperture 136 to the mixing portion 124 at a controlled rate back into the rear portion 15 of the blood sample 12.

The biological fluid collection device 100 meters the front portion 13 of the blood sample 12 with the additive front 184 back into the rear portion 15 of the blood sample 12 to achieve a single flow stream, i.e., the stabilized biological sample, with the sample stabilizer 14 distributed along the single flow stream.

After a stabilized biological sample with head-to-tail uniformity is produced by the biological fluid collection device 100, the stabilized biological sample flows to the outlet portion 122. At this time, the biological fluid collection device 100 may be engaged with a blood testing device or point-of-care testing device for closed transfer of a portion of the stabilized biological sample from the biological fluid collection device 100 to the blood testing device or point-of-care testing device. The blood testing device is adapted to receive the stabilized biological sample to analyze the stabilized biological sample and obtain test results.

A biological fluid collection device 100 of the present disclosure rapidly captures and redistributes a concentrated flow front throughout the lower concentration flow tail. This is of particular interest because many prior art devices have problems uniformly distributing dry additive in small sample volumes. At these volumes, a biological fluid collection device 10 of the present disclosure takes advantage of capillary forces to preferentially fill the mixer's center chamber (volume=<10-1000 µL).

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A biological fluid collection device, comprising:
an inlet portion adapted to receive a biological fluid therethrough;
an outlet portion;
an outer wall spanning the inlet portion and the outlet portion;
an inner wall disposed within the outer wall and spaced from the outer wall, the inner wall defining a central chamber therein and including a first end and a second end oppositely disposed from the first end, the first end defining an opening of the central chamber, wherein the opening is positioned adjacent to and in fluid communication with the inlet portion and is configured for receiving a first portion of the biological fluid entering through the inlet portion and the second end defines an exit aperture, wherein the first portion of the biological fluid moves along a linear path from the inlet portion through the opening, into the central chamber, and to the second end;
a flow channel disposed between the outer wall and the inner wall, the flow channel surrounding at least a portion of the central chamber, the flow channel having a first end in fluid communication with the inlet portion and configured for receiving a second portion of the biological fluid entering through the inlet portion, the flow channel configured to divert the second portion of the biological fluid around the central chamber;

a mixing portion disposed between the second end of the inner wall and the outlet portion, wherein the exit aperture is in fluid communication with the mixing portion; and a sample stabilizer disposed within an interior portion of the outer wall between the inlet portion and the first end of the inner wall, wherein the sample stabilizer is configured to mix with the biological fluid entering through the inlet portion to create a first front and a second front, wherein the first front is configured to enter through the opening of the central chamber and configured to flow through the central chamber and exit through the exit aperture and the second front is configured to flow through the flow channel, wherein a diameter of the opening of the central chamber is greater than a diameter of the exit aperture causing the first front to exit the central chamber at a slower rate than the second front exiting the flow channel, and wherein the first front exiting through the exit aperture and the second front exiting the flow channel are mixed in the mixing portion.

2. The biological fluid collection device of claim 1, wherein a distance between the inner wall and the outer wall is greater than a diameter of the exit aperture.

3. The biological fluid collection device of claim 1, wherein the opening at the first end defines a first cross-sectional area and the exit aperture defines a second cross-sectional area, wherein the first cross-sectional area is greater than the second cross-sectional area.

4. The biological fluid collection device of claim 1, wherein the inner wall is secured to the outer wall via a connection portion.

5. The biological fluid collection device of claim 1, wherein the outer wall at the inlet portion has a first diameter, and a first portion of the outer wall between the inlet portion and the first end of the inner wall has a second diameter, the second diameter is less than the first diameter.

6. The biological fluid collection device of claim 5, wherein a second portion of the outer wall adjacent the inner wall has a third diameter, the third diameter is greater than the second diameter.

7. The biological fluid collection device of claim 1, wherein the biological fluid sample comprises a blood sample and the inlet portion is adapted to receive the blood sample therein.

8. The biological fluid collection device of claim 1, wherein the biological fluid collection device is configured such that the location of the sample stabilizer within the collection device creates the first front within a front portion of the blood sample.

9. The biological fluid collection device of claim 8, wherein the biological fluid collection device is configured to cause the first front to flow into the central chamber of the inner wall and a rear portion of the blood sample creating the second front to flow into the flow channel.

10. The biological fluid collection device of claim 9, wherein the biological fluid collection device is configured to cause the front portion of the blood sample with the first front to flow through the exit aperture to the mixing portion at a controlled rate back into the rear portion of the blood sample.

11. The biological fluid collection device of claim 10, wherein the biological fluid collection device is configured to cause the front portion of the blood sample with the first front to flow through the exit aperture to the mixing portion back into the rear portion of the blood sample to effectuate metered mixing of the sample stabilizer within the front portion of the blood sample and the rear portion of the blood sample.

12. The biological fluid collection device of claim 1, further comprising a material including pores and disposed within the interior portion of the outer wall, and the sample stabilizer comprises a dry anticoagulant powder within the pores of the material.

13. The biological fluid collection device of claim 12, wherein the material is an open-cell foam.

14. The biological fluid collection device of claim 1, wherein the sample stabilizer comprises a dry anticoagulant powder.

15. The biological fluid collection device of claim 1, further comprising fins to promote rotational mixing.

16. The biological fluid collection device of claim 1, wherein the inner wall defines a side exit aperture.

17. A biological fluid collection device, comprising:
an inlet portion adapted to receive a biological fluid therethrough;
an outlet portion;
an outer wall spanning the inlet portion and the outlet portion, the outer wall including a top wall and a bottom wall;
a first inner wall disposed within the outer wall and spanning the top wall and the bottom wall, the first inner wall including a first inner wall first end positioned adjacent to and in fluid communication with the inlet portion and a first inner wall second end oppositely disposed from the first inner wall first end;
a second inner wall disposed within the outer wall and spanning the top wall and the bottom wall, the second inner wall including a second inner wall first end positioned adjacent to and in fluid communication with the inlet portion and a second inner wall second end oppositely disposed from the second inner wall first end;
a first flow channel disposed between a first portion of the outer wall and the first inner wall, the first flow channel in fluid communication with the inlet portion;
a second flow channel disposed between a second portion of the outer wall and the second inner wall, the second flow channel in fluid communication with the inlet portion, wherein the first inner wall first end is spaced a first distance from the second inner wall first end to define an opening and the first inner wall second end is spaced a second distance from the second inner wall second end, the second distance being less than the first distance and wherein the second distance defines an exit aperture;
a mixing portion disposed between the first inner wall second end and the outlet portion; and
a sample stabilizer disposed within a portion of an interior of the outer wall between the inlet portion and the opening, wherein the first inner wall and the second inner wall together define a chamber therebetween, wherein the opening is in fluid communication with the chamber and the chamber is in fluid communication with the inlet portion at a location that is adjacent to the inlet portion, wherein the sample stabilizer is configured to mix with the biological fluid entering the inlet portion to create a first front and a second front, wherein the first front is configured to enter through the opening and flow through the chamber and exit through the exit aperture and the second front is configured to flow through at least one of the first flow channel and the second flow channel such that the first front exiting through the exit aperture and the second front are mixed in the mixing portion.

18. The biological fluid collection device of claim 17, wherein the first portion of the outer wall comprises a first sidewall and the second portion of the outer wall comprises a second sidewall.

19. The biological fluid collection device of claim 17, wherein the biological fluid comprises a blood sample and the inlet portion is adapted to receive the blood sample therein.

20. The biological fluid collection device of claim 19, wherein the fluid collection device is configured such that the sample stabilizer is located adjacent to the inlet portion to enable mixing with the blood sample received within the inlet portion.

21. The biological fluid collection device of claim 20, wherein the biological fluid collection device is configured such that the location of the sample stabilizer within the collection device creates the first front within a front portion of the blood sample.

22. The biological fluid collection device of claim 21, wherein the biological fluid collection device is configured to cause the first front to flow into the chamber and a rear portion of the blood sample creating the second front to flow into the first flow channel and the second flow channel.

23. The biological fluid collection device of claim 22, wherein the biological fluid collection device is configured to cause the front portion of the blood sample with the first front to flow through the exit aperture to the mixing portion at a controlled rate back into the rear portion of the blood sample.

24. The biological fluid collection device of claim 23, wherein the biological fluid collection device is configured to cause the front portion of the blood sample with the first front to flow through the exit aperture to the mixing portion back into the rear portion of the blood sample to effectuate metered mixing of the sample stabilizer within the front portion of the blood sample and the rear portion of the blood sample.

25. The biological fluid collection device of claim 17, further comprising a material including pores and disposed within the interior portion of the outer wall, and the sample stabilizer comprises a dry anticoagulant powder within the pores of the material.

26. The biological fluid collection device of claim 25, wherein the material is an open cell foam.

27. The biological fluid collection device of claim 17, wherein the sample stabilizer comprises a dry anticoagulant powder.

* * * * *